United States Patent
Chandrasekaran et al.

(10) Patent No.: US 12,410,113 B2
(45) Date of Patent: Sep. 9, 2025

(54) SANDALWOOD-TYPE FRAGRANCE COMPOUNDS

(71) Applicant: SYMRISE AG, Holzminden (DE)

(72) Inventors: Vijayanand Chandrasekaran, Holzminden (DE); Bernd Hoelscher, Halle (DE); Eva Kiermasch, Holzminden (DE)

(73) Assignee: SYMRISE AG, Holzminden (DE)

( * ) Notice: Subject to any disclaimer, the term of this patent is extended or adjusted under 35 U.S.C. 154(b) by 754 days.

(21) Appl. No.: 17/614,238

(22) PCT Filed: Jun. 12, 2020

(86) PCT No.: PCT/EP2020/066394
§ 371 (c)(1),
(2) Date: Nov. 24, 2021

(87) PCT Pub. No.: WO2020/249794
PCT Pub. Date: Dec. 17, 2020

(65) Prior Publication Data
US 2022/0220051 A1 Jul. 14, 2022

(30) Foreign Application Priority Data

Jun. 13, 2019 (WO) ................ PCT/EP2019/065629

(51) Int. Cl.
| C07C 29/147 | (2006.01) |
| C07C 17/16 | (2006.01) |
| C07C 45/41 | (2006.01) |
| C07C 45/62 | (2006.01) |
| C07C 67/343 | (2006.01) |
| C11B 9/00 | (2006.01) |

(52) U.S. Cl.
CPC ............ *C07C 29/147* (2013.01); *C07C 17/16* (2013.01); *C07C 45/41* (2013.01); *C07C 45/62* (2013.01); *C07C 67/343* (2013.01); *C11B 9/0019* (2013.01)

(58) Field of Classification Search
CPC ....... C07C 29/147; C07C 17/16; C07C 45/41; C07C 45/62; C07C 67/343; C07C 33/12; C07C 2601/02; C07C 2601/08; C07C 2601/10; C11B 9/0019
See application file for complete search history.

(56) References Cited

U.S. PATENT DOCUMENTS 4,610,813 A 9/1986 Schulte-Elte et al.

FOREIGN PATENT DOCUMENTS

| EP | 0155591 A2 | 9/1985 | |
| EP | 0694520 A1 | 1/1996 | |
| EP | 0801049 A2 | 10/1997 | |
| EP | 2411355 B1 | 1/2013 | |
| JP | 2018131402 A | * 8/2018 | ............ C07C 17/16 |
| WO | WO-93/21142 A1 | 10/1993 | |
| WO | WO-2008/052379 A2 | 5/2008 | |
| WO | WO-2016/074118 A1 | 5/2016 | |

OTHER PUBLICATIONS

Chang et al., QSAR of alpha-campholenic derivatives with sandalwood odor, and molecular design(Monatsh Chem. (2010) 141:953-959).*
Arctander, "Perfume and Flavor Chemicals," front matter and table of contents, self-publication (1969).
International Search Report and Written Opinion from International Application No. PCT/EP2020/066394 dated Aug. 11, 2020.
Marshall et al., "The Reduction of Malonic Enolates with Lithium Aluminum Hydride," J. Org. Chem. 32(1):113-118 (1967).
Schulze et al., "α-Methylated Fencholenic and α-Campholenic Aldehyde—Synthesis and Reactions," J. prakt. Chem. 335:687-693 (1993).
Wenkert et al., "A Method of Synthesis of β-Methylfurans and α-Methylene and β-Methylene γ-Lactones. Two Menthofuran Syntheses," Journal of the American Chemical Society 99(14):4778-4782 (1977).
Office Action (with Translation) from Indian Application No. 202117055650 dated Feb. 1, 2023.

* cited by examiner

*Primary Examiner* — Jafar F Parsa
(74) *Attorney, Agent, or Firm* — MARSHALL, GERSTEIN & BORUN LLP

(57) ABSTRACT

The present invention relates to novel fragrance compounds derived from campholenic aldehyde according to general Formula (II) or from the cyclopropanated campholenic aldehyde according to general Formula (III), or to compositions comprising one or more such fragrance compounds. The invention also relates to methods for preparing these compounds and to particular intermediates which are used in the preparation processes according to the present invention. It also pertains to a method for producing, enhancing or modifying a sandalwood odor in a formulation. The invention also relates to the use of such compounds or fragrance compositions comprising one or more compounds according to the invention as an odorant or for improving the fixation of a fragrance compound or a composition comprising a fragrance compound or for preparing perfumed products. Finally, the invention relates to corresponding perfumed products.

12 Claims, No Drawings

SANDALWOOD-TYPE FRAGRANCE COMPOUNDS

CROSS-REFERENCE TO RELATED APPLICATIONS

This is a U.S. National Phase of International Application No. PCT/EP2020/066394, filed Jun. 12, 2020, which claims priority to International Application No. PCT/EP2019/065626, filed Jun. 13, 2019, the contents of which are incorporated herein by reference.

FIELD OF THE INVENTION

The present invention relates to novel fragrance compounds derived from campholenic aldehyde according to general Formula (II) or from the cyclopropanated campholenic aldehyde according to general Formula (III), or to compositions comprising one or more such fragrance compounds. The invention also relates to methods for preparing these compounds and to particular intermediates which are used in the preparation processes according to the present invention. It also pertains to a method for producing, enhancing or modifying a sandalwood odor in a formulation. The invention also relates to the use of such compounds or fragrance compositions comprising one or more compounds according to the invention as an odorant or for improving the fixation of a fragrance compound or a composition comprising a fragrance compound or for preparing perfumed products. Finally, the invention relates to corresponding perfumed products.

PRIOR ART

There is sustained interest within the fragrance industry in developing new fragrance substances in order to enable the creation of new perfume oils, for both alcoholic and functional perfumery. Compounds with a woody odor are indispensable components in the fragrance industry. One particularly valuable class of these woody fragrance substances are compounds with a sandalwood odor. Compounds with a sandalwood odor are frequently characterised structurally by a 4-(2,2,3-trimethyl-cyclopent-3-enyl)-butan-1-ol parent structure, wherein the butan-1-ol side chain can be saturated or monounsaturated and monomethyl- or polymethyl-substituted. Representatives of this class of fragrance substances include 2-methyl-4-(2',2',3'-trimethyl-3'-cyclopenten-1'-yl)-butan-1-ol (i) (Brahmanol®, Symrise GmbH & Co. KG), 2-ethyl-4-(2',2',3'-trimethyl-3'-cyclopenten-1'-yl)-2-buten-1-ol (ii) (Sandranol®, Symrise GmbH & Co. KG), 3-methyl-5-(2',2',3'-trimethyl-3'-cyclopenten-1'-yl)-4-penten-2-ol (iii) (Ebanol®, Givaudan S.A.) and 3,3-dimethyl-5-(2',2',3'-trimethyl-3'-cyclopenten-1'-yl)-4-penten-2-ol (iv) (Polysantol®, Firmenich S.A.):

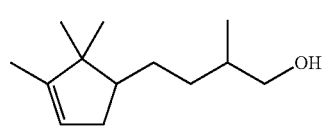

(i)

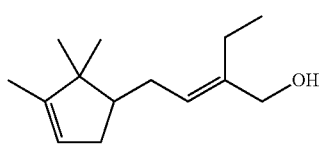

(ii)

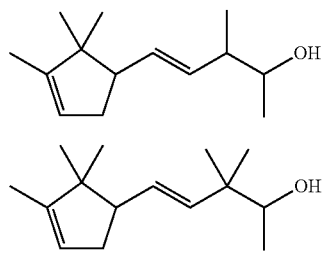

(iii)

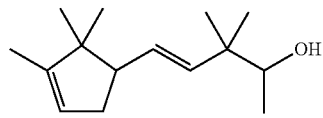

(iv)

The compounds of Formulae (i) to (iv) have a sandalwood odor which varies among the compounds (a) in strength and (b) in further odor aspects of the individual compounds (i) to (iv).

U.S. Pat. No. 4,610,813 discloses hydroxylic derivatives of campholenic aldehyde, which fall within general Formula (v):

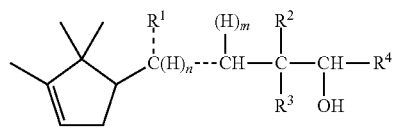

Formula (v)

The compounds of Formula (v) possess useful odorous properties and are used for preparing perfumes and perfumed products.

EP 0 801 049 A2 discloses odorants, derived from campholenic aldehyde, which are cyclopentanebutanol derivatives of general Formula (vi):

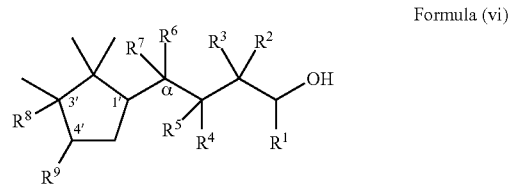

Formula (vi)

In Formula (vi), $R^1$ to $R^7$ are independently H, —$CH_3$ (methyl group) or —$C_2H_5$ (ethyl group), $R^8$ and $R^9$ represent methylene (—$CH_2$—) or a single bond, or $R^1$ and $R^2$ represent —$(CH_2)_n$—, with n being 3 or 4, or $R^3$ and $R^5$ or $R^5$ and $R^7$ represent methylene or a single bond. The presence of at least one cyclopropane ring in the molecule is compulsory, and the side chain can be saturated or can contain one double bond in the position α,ß or ß,γ. Representatives of this class of fragrance substances include Pashminol® or Javanol® (Givaudan).

The compounds are obtained by a process comprising:
(a) mono- or dicyclopropanating a compound of Formula (vii), (viii) or (ix):

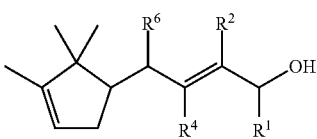

Formulae (vii), (viii) and (ix)

-continued

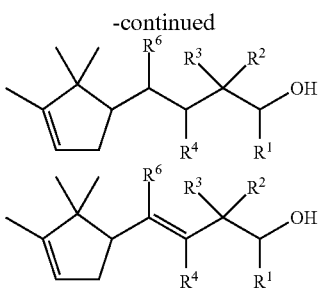

or
(b) reducing a compound of Formula (x), (xi) or (xii):

Formulae (x), (xi) and (xii)

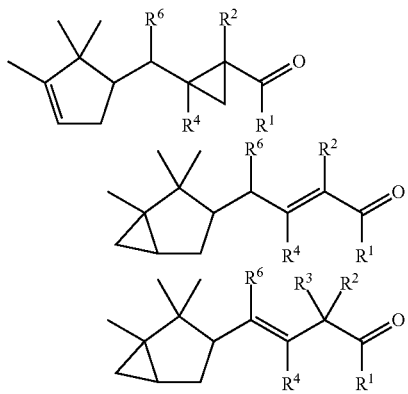

The alcohols of general Formula (vi) exhibit various woody odor aspects. Most of them exert a sandalwood odor, but some are also simply woody/amber-like. Of the above compounds, [1-methyl-2-(1,2,2-trimethyl-bicyclo[3.1.0] hex-3-yl-methyl-)cyclopropyl-]methanol has the most natural, the strongest and the most persistent sandalwood odor.

WO 2008/052379 A2 discloses cyclopropanated 2,2,3-trimethylcyclopentane derivatives according to general Formula (xiii)

Formula (xiii)

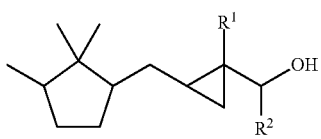

wherein $R^1$ is methyl or ethyl; and $R^2$ is hydrogen, methyl or ethyl, and a method for their production.

The compounds of general Formula (xiii) possess a natural sandalwood oil odor profile. Representatives of this class of fragrance substances include Pashminol® or Javanol® (Givaudan).

In view of the compounds already existent, the impression may be given that there is a sufficiently broad spectrum of sandalwood fragrant raw materials.

In reality, it has become apparent that this is not the case. While it may be true to say that each of the prior-known compounds is able to confer a sandalwood note to the compositions into which it is incorporated, the specific effects achieved vary widely from one compound to the next. Their diffusiveness, for example, as well as their substantivity can also vary as a function of the particular application for which they are destined. Though they have all been defined as sandalwood-type compounds, no two possess an identical odor character. Experts recognise that in fact the typical sandalwood oil note is but the result of a number of different odorous notes reminiscent in turn of santalol, cedarwood oil or guaiac wood oil, or of sweet, balsamic, slightly ambery, spicy or animal notes or even of those milky notes reminiscent of freshly boiled milk.

It does not therefore come as a surprise to find that none of the known compounds suggested by the prior art can, when taken alone, replace natural sandalwood oil, each of them but contributing to a greater or lesser extent to one or other of its specific partial characters. This fact may sound astonishing when looking at the analogy, from the point of view of their structure, presented by the above-cited known derivatives of camphorenic aldehyde. This confirms once again the character of uncertainty which surrounds any speculation in the field of aroma chemicals where no known theory allows the molecular structure of a given chemical and its odor properties to be validly correlated.

As a result of this situation, there is a permanent need to develop novel compounds with sandalwood fragrance character in order to enlarge the perfumer's palette.

The object of the present invention is thus to provide new sandalwood fragrance compounds which have a low odorous threshold value and, with regard to some or all of its secondary properties, is equal or even superior to the sandalwood fragrance substances known from the prior art. Desired secondary properties in this connection are in particular elevated tenacity, elevated impact, elevated substantivity, the property of acting as a fixative and the ability to create a good blooming effect.

It has now been surprisingly found that the new cyclopentanebutanol derivatives according to the general Formula (I) comprising at least one cyclopropane substituent attached to the butyl chain in position C2 or C4 or at least one alkenyl group attached to the butyl chain in position C2 or C4 have a pronounced natural and intense sandalwood oil odor and produce excellent fragrances.

SUMMARY OF THE INVENTION

In a first aspect, the present invention relates to a compound of general Formula (I):

Formula (I)

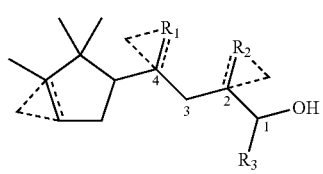

wherein
$R_1$ represents H, an alkyl or an alkenyl group,
$R_2$ represents an alkyl or an alkenyl group, and
$R_3$ represents H or an alkyl group;
wherein at the position of the dotted lines there is optionally a C=C double bond or a cyclopropane ring; and
wherein the butyl chain C1 to C4 is either saturated or is unsaturated and contains one double bond in position C2/C3 or C3/C4;

wherein the compound comprises either
- at least one cyclopropane substituent attached to the butyl chain in position C2 or C4; or
- at least one alkenyl group attached to the butyl chain in position C2 or C4, wherein if the alkenyl group is attached to the butyl chain in position C4, the butyl chain comprises a C=C double bond in position C2/C3 or a further alkenyl group in position C2;

or its stereoisomers, in particular enantiomers; or relates to a compound of general Formula (VI):

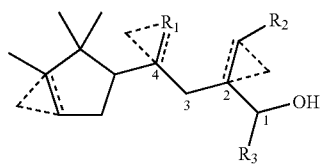

Formula (VI)

wherein
$R_1$ represents H, an alkyl or an alkenyl group,
$R_2$ represents H or an alkyl, and
$R_3$ represents H or an alkyl group;
wherein at the position of the dotted lines there is optionally a C=C double bond or a cyclopropane ring; and
wherein the butyl chain C1 to C4 is either saturated or is unsaturated and contains one double bond in position C2/C3 or C3/C4;
wherein the compound comprises either
- at least one cyclopropane substituent attached to the butyl chain in position C2 or C4; or
- at least one alkenyl group attached to the butyl chain in position C2 or C4, wherein if the alkenyl group is attached to the butyl chain in position C4, the butyl chain comprises a C=C double bond in position C2/C3 or wherein if the alkenyl group is attached to the butyl chain in position C2, the butyl chain comprises a C=C double bond in position C3/C4; or
- an alkyl group attached to the butyl chain in position C2 and C4, wherein the butyl chain comprises a C=C double bond in position C2/C3;

or its stereoisomers, in particular enantiomers.

In a second aspect, the present invention relates to methods for producing a compound of general Formula (I) or of general Formula (VI) according to Claims 6, 7, 8 or 9.

In a third aspect, the present invention relates to a method of producing, enhancing or modifying a sandalwood odor in a formulation.

In another aspect, the present invention relates to the use of a compound according to the present invention or a composition comprising a compound according to the invention as an odorant.

In yet another aspect, the present invention relates to the use of a compound according to the present invention or a composition comprising a compound according to the invention for improving the fixation of a fragrance compound or a composition comprising a fragrance compound or as an ingredient for preparing perfumed products.

Finally, the present invention relates to a perfumed product comprising a compound according to the present invention, in an effective amount, and a carrier or substrate.

In yet another aspect, the present invention relates to a compound according to general Formula (IV):

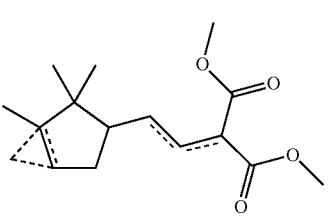

Formula (IV)

a method for preparing a compound of general Formula (IV) and its use for preparing compound A or B or their stereoisomers, in particular their enantiomers.

DETAILED DESCRIPTION OF THE INVENTION

In accordance with the invention, the above object is achieved by a compound of general Formula (I):

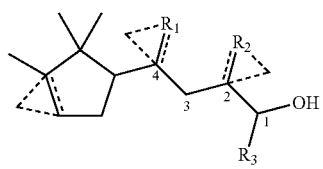

Formula (I)

wherein
$R_1$ represents H, an alkyl or an alkenyl group,
$R_2$ represents an alkyl or an alkenyl group, and
$R_3$ represents H or an alkyl group;
wherein at the position of the dotted lines there is optionally a C=C double bond or a cyclopropane ring; and
wherein the butyl chain C1 to C4 is either saturated or is unsaturated and contains one double bond in position C2/C3 or C3/C4;
wherein the compound comprises either
- at least one cyclopropane substituent attached to the butyl chain in position C2 or C4; or
- at least one alkenyl group attached to the butyl chain in position C2 or C4, wherein if the alkenyl group is attached to the butyl chain in position C4, the butyl chain comprises a C=C double bond in position C2/C3 or a further alkenyl group in position C2;

or its stereoisomers, in particular enantiomers; or relates to a compound of general Formula (VI):

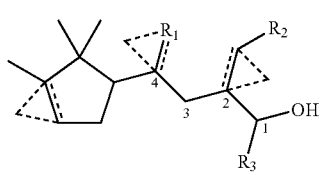

Formula (VI)

wherein
$R_1$ represents H, an alkyl or an alkenyl group,
$R_2$ represents H or an alkyl, and
$R_3$ represents H or an alkyl group;

wherein at the position of the dotted lines there is optionally a C=C double bond or a cyclopropane ring; and
wherein the butyl chain C1 to C4 is either saturated or is unsaturated and contains one double bond in position C2/C3 or C3/C4;
wherein the compound comprises either
at least one cyclopropane substituent attached to the butyl chain in position C2 or C4; or
at least one alkenyl group attached to the butyl chain in position C2 or C4, wherein if the alkenyl group is attached to the butyl chain in position C4, the butyl chain comprises a C=C double bond in position C2/C3 or wherein if the alkenyl group is attached to the butyl chain in position C2, the butyl chain comprises a C=C double bond in position C3/C4; or
an alkyl group attached to the butyl chain in position C2 and C4, wherein the butyl chain comprises a C=C double bond in position C2/C3;
or its stereoisomers, in particular enantiomers.

The butyl chain C1 to C4 in the general Formula (I) or in the general Formula (VI) is defined as a four-carbon chain. In the general Formula (I) or in the general Formula (VI), the butyl chain is the n-butyl chain —$CH_2$—$CH_2$—$CH_2$—$CH_2$— which connects at one of the two terminal carbon atoms to the cyclopentane ring and on the other terminal carbon atom to an —OH group.

In the general Formula (I) $R_1$ represents H, an alkyl or an alkenyl group; $R_2$ represents an alkyl or an alkenyl group; and/or $R_3$ represents H or an alkyl group; independently from each other.

In the general Formula (VI) $R_1$ represents H, an alkyl or an alkenyl group; $R_2$ represents H or an alkyl; and/or $R_3$ represents H or an alkyl group; independently from each other.

Preferably, the alkyl group is selected from the group consisting of a methyl or a higher straight or branched alkyl chain such as ethyl, propyl, n-butyl or iso-butyl group. More preferably, the alkyl group is a methyl or ethyl group.

In general Formula (I) or in general Formula (VI) at the position of the dotted lines in the butyl chain C1 to C4 or in the cyclopentane ring, there is optionally a C=C double bond or a cyclopropane ring. The dotted lines are the most concise way of expressing these options in the structural formula. The three dotted line positions in the general Formula (I) or in the general Formula (VI) may stand optionally for a double bond at these positions, or a cyclopropane ring at these positions, or no extra function. In the alternative case, that there is no extra function at any of these positions, the dotted lines can be ignored, and we simply have a single bond, which forms a C≡C bond in the cyclopentane ring, or a C4-R1 single bond or a C2-R2 single bond, respectively. This meaning is also evident from the examples.

The substituents $R_1$, $R_2$ and $R_3$ can have the functionalities indicated above. It was found that the substituent at the C2 position in the butyl chain C1 to C4 ($R_2$ in general Formula (I)) should preferably have an $R_2$ functionality that is other than "—H", i.e. there should not be a C—H bond with —H as the $R_2$ functionality. These compounds with $R_2$ other than —H achieve a typical sandalwood fragrance. Thus, the C2 position in general Formula (I) may preferably have an alkyl group for $R_2$, such as —$CH_3$, or a higher straight or branched alkyl chain. In general Formula (VI) the substituent at the C2 position may be an alkyl group, such as —CH3, or a higher straight or branched alkyl chain together with $R_2$ which represents H or an alkyl group, preferably methyl. However, it was also found that this position may have a C=C double bond giving an alkenyl group or a cyclopropane ring, both of which were found to also work well to give the sandalwood fragrance.

When the dotted lines in the butyl chain C1 to C4 at position C2 or C4 of general Formula (I) represent a double bond, then $R_1$ or $R_2$ independently represents an alkenyl group.

When the dotted lines in the butyl chain C1 to C4 at position C2 or C4 of general Formula (VI) represent a double bond, then $R_1$ represents an alkenyl group, or the substituent at C2 position of the butyl chain is an alkenyl group.

Preferably, the alkenyl group is an ethenyl, propenyl or butenyl group. More preferably, the alkyenyl group is an ethenyl group (—$CH_2$).

In an alternative embodiment, the dotted lines in the butyl chain C1 to C4 at position C2 or C4 of general Formula (I) or general Formula (VI) can also represent a cyclopropane ring substituent, as the $R_1$ or $R_2$ substituent in general Formula (I) or as the $R_1$ substituent or substituent at position C2 in general Formula (VI), which is attached to the butyl chain C1 to C4. In this case, one of the carbon atoms of the butyl chain forms a corner of the cyclopropane ring.

In the case of a cyclopropane ring, the term "attached to the butyl chain C1 to C4" of general Formula (I) or of general Formula (VI) in the context of the present invention means that only one carbon atom of the cyclopropane ring is part of the butyl chain C1 to C4 or that only one of the C atoms of the butyl chain forms part of the ring, or in other words the attachment C position of the butyl chain connects directly with the other two carbon atoms of the cyclopropane ring. Therefore, preferably, the cyclopropane ring is not part of the butyl chain such that two of the carbon atoms of the butyl chain form ring members. This excludes compounds where two carbon atoms of the cyclopropane ring are part of the butyl chain C1 to C4, in particular in position C2 and C3 of the butyl chain.

In a further variant, the cyclopentane ring has a C=C double bond in position C3/C4 of the cyclopentane ring, as depicted by the dotted lines in general Formula (I) or in general Formula (VI).

In yet another variant, the cyclopentane ring is monocyclopropanated, as depicted by the dotted lines in general Formula (I) or in general Formula (VI). In this case, there is preferably a cyclopropane ring formed with two corners from the C atoms in position C3/C4 of the cyclopentane ring.

In the compound of general Formula (I) or of general Formula (VI) the butyl chain C1 to C4 can be either saturated or unsaturated.

In a preferred variant the butyl chain C1 to C4 of the compound of general Formula (I) or of general Formula (VI) is unsaturated and contains one C=C double bond in position C2/C3 or one C=C double bond in position C3/C4.

In a preferred variant, the compound of general Formula (I) or of general Formula (VI) comprises at least one cyclopropane substituent attached to the butyl chain C1 to C4. In this case, one of the carbon atoms of the butyl chain forms a corner of the cyclopropane ring or only one carbon atom of the cyclopropane ring is part of the butyl chain C1 to C4.

In yet another preferred variant of general Formula (I), the at least one cyclopropane substituent is attached to the butyl chain in position C2 or C4 as the $R_1$ or $R_2$ substituent. It is possible that both C2 and C4 positions of the butyl chain have a cyclopropane substituent.

In yet another preferred variant of general Formula (VI), the at least one cyclopropane substituent is attached to the butyl chain at position C2 or C4 as the $R_1$ substituent or as substituent at C2 position. It is possible that both C2 and C4 positions of the butyl chain have a cyclopropane substituent.

In a more preferred variant, the compound of general Formula (I) or of general Formula (VI) comprises at least one cyclopropane substituent attached to the butyl chain C1 to C4 in position C2 as the $R_2$ substituent or as the substituent at C2 position.

In a more preferred variant, the compound of general Formula (I) or of general Formula (VI) comprises at least one cyclopropane substituent attached to the butyl chain C1 to C4 in position C4 as the $R_1$ substituent.

Preferably, if the cyclopropane substituent is attached to the butyl chain in position C2 or C4, then the cyclopentane ring contains a C=C double bond, preferably in position C3/C4 of the cyclopentance ring, or the cyclopentane ring is monocyclopropanated, preferably in position C3/C4 of the cyclopentane ring.

Alternatively, the compound of general Formula (I) or of general Formula (VI) comprises at least one alkenyl group attached to the butyl chain C1 to C4 in position C2 or C4.

If the alkenyl group is attached to the butyl chain in position C2, the butyl chain can either be saturated or unsaturated, preferably in C2/C3 position.

If the alkenyl group is attached to the butyl chain in position C4, the butyl chain comprises either a C=C double bond in the butyl chain, preferably in C2/C3 position, or a further alkenyl group, preferably attached in position C2 to the butyl chain.

In a more preferred variant, the compound of general Formula (I) or of general Formula (VI) comprises at least one alkyenyl group attached to the butyl chain in position C2.

In a still further preferred variant, the compound of general Formula (I) or of general Formula (VI) comprises at least one alkenyl group attached to the butyl chain in position C2 and a cyclopropanated cyclopentane ring.

Preferably, if the alkenyl substituent is attached to the butyl chain in position C2 or C4, then the cyclopentane ring contains a C=C double bond, preferably in position C3/C4 of the cyclopentance ring, or the cyclopentane ring is monocyclopropanated, preferably in position C3/C4 of the cyclopentane ring.

In a more preferred variant, the compound of general Formula (I) or of general Formula (VI) comprises an alkenyl group attached to the butyl chain in both position C2 and C4.

In a still further preferred variant, the compound of general Formula (I) or of general Formula (VI) comprises at least three C=C double bonds in the molecule.

In a still further preferred variant, the compound of general Formula (I) or of general Formula (VI) comprises an allylic system in position C2 and C4 of the butyl chain and a cyclopropanated cyclopentane ring.

In a still further preferred variant, the compound of general Formula (VI) comprises at least one alkenyl group attached to the butyl chain in position C2 and/or C4, wherein if the alkenyl group is attached to the butyl chain in position C4, the butyl chain comprises a C=C double bond in position C2/C3 or wherein if the alkenyl group is attached to the butyl chain in position C2, the butyl chain comprises a C=C double bond in position C3/C4. In a most preferred variant, the alkenyl group attached to the butyl chain in position C2 is substituted by an alkyl group.

In a still further preferred variant, the compound of general Formula (VI) comprises an alkyl group attached to the butyl chain at position C2 and/or C4, wherein the butyl chain comprises a C=C double bond at position C2/C3. Additionally, the alkyl groups at positions C2 and C4 are either the same or different. Most preferred are compounds of general Formula (VI), in which at position C2 the alkyl substituent is a higher straight or branched alkyl chain with two or more C atoms, i.e. ethyl, propy or butyl group, together with $R_2$ which represents H or an alkyl group, preferably methyl.

Furthermore, preferably the compounds of general Formula (I) do not comprise the compound 2-methyl-4-(2',2', 3'-trimethyl-3'-cyclopenten-1'-yl)-4-penten-1-ol or its stereoisomers

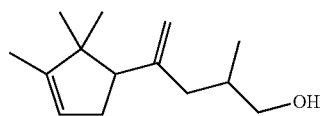

Common characterising feature of the compounds of general Formula (I) is, that they comprise at least one cyclopropane function attached to the butyl chain C1 to C4, preferably in position C2 or C4; or at least one alkenyl group attached to the butyl chain C1 to C4, preferably in position C2 or C4. Typically, the compounds also contain a hydroxy group, preferably attached the butyl chain in C1 position.

In a preferred variant, the compounds of general Formula (I) or of general Formula (VI) comprise at least three functional groups selected from the groups consisting of:
(a) cyclopropane rings
(b) double bonds.

Preferably one of the functional groups is in the cyclopentane ring and two other functional groups are in or attached to the butyl chain C1 to C4.

The compounds of general Formula (I) or of general Formula (VI) are derivatives derivable from hydroxylic campholenic aldehyde (cyclopentanebutanol) or hydroxylic campholenic aldehyde with a cyclopropanated cyclopentane ring.

It is known that campholenic aldehyde (campholene aldehyde) according to the following formula may comprise a chiral centre and as such may exist as isomerically pure forms or in any mixture of its stereoisomers, in particular enantiomers, as a function of the particular isomerism of the alpha-pinene used as the starting material for preparing it. The asterisk in the following formula denotes for the chiral center; the stereoisomeric forms are (−) campholeic aldehyde or (+) campholeic aldehyde.

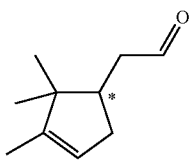

This implies that the compounds according to the present invention derived from campholenic aldehyde (campholene aldehyde) can also occur in different stereoisomeric forms. Consequently, whenever reference is made in the present description to a compound of general Formula (I) or of general Formula (VI), this is deemed to refer to all stereoisomers, in particular to all enantiomers, indifferently to the isomerically pure stereoisomers or mixtures of any of their stereoisomers. For economic reasons it is preferred to use the compounds as mixtures of their stereoisomers, in particular mixtures of their enantionamers.

The compounds of general Formula (I) or of general Formula (VI) are thus preferably present in the form of:
(a) a pure optically active enantiomer;
(b) a racemic mixture of the enantiomers; or
(c) an optically active mixture of various enantiomers.

In a preferred variant of the present invention, the compound of general Formula (I) is selected from the group consisting of the following compounds specified in Table 1

TABLE 1

| Compound No. | Structure |
|---|---|
| A | 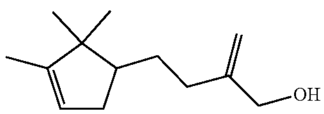 |
| A1 | 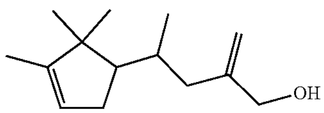 |
| B | 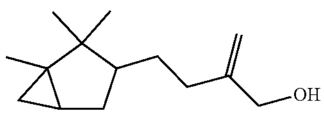 |
| B1 | 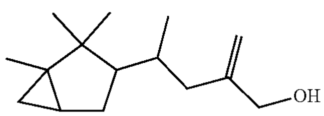 [SMILES: C=C(CO)CC(C)C1CC2CC2(C)C1(C)C] |
| C | 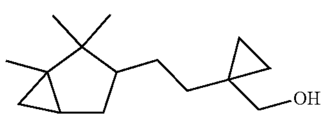 [SMILES: CC1(C)C(CCC2(CO)CC2)CC2CC21C] |
| D | 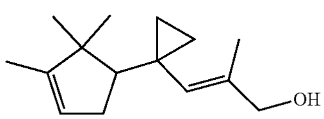 [SMILES: CC1=CCC(C2(/C=C(\C)CO)CC2)C1(C)C] |
| E | 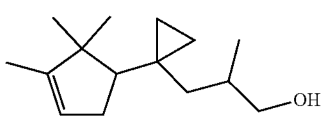 [SMILES: CC1=CCC(C2(CC(C)CO)CC2)C1(C)C] |
| F | 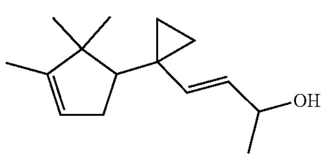 [SMILES: CC1=CCC(C2(/C=C/C(C)O)CC2)C1(C)C] |
| G | 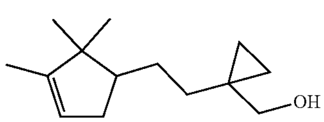 |
| I | 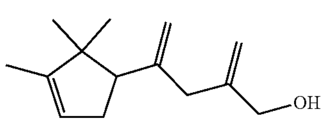 |

TABLE 1-continued

| Compound No. | Structure |
|---|---|
| J | 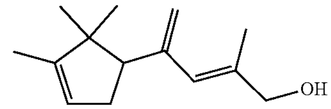 |
| K | 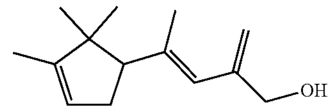 |
| L | | and their stereoisomers, preferably enantiomers, and mixtures of these compounds.

In a preferred variant of the present invention, the compound of general Formula (VI) is selected from the group consisting of the following compounds specified in Table 2

TABLE 2

| Compound No. | Structure |
|---|---|
| M | 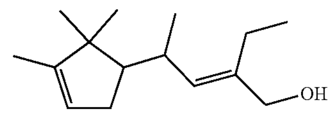 [SMILES: CC/C(=C\C(C)C1CC=C(C)C1(C)C)CO] |
| N | 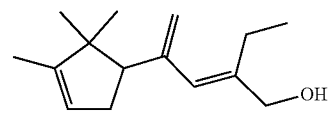 [SMILES: C=C(/C=C(\CC)CO)C1CC=C(C)C1(C)C] |
| O | | and their stereoisomers, preferably enantiomers, and mixtures of these compounds.

The structure of the above preferred compounds according to general Formula (I) or general Formula (VI) of the invention has been proven by their NMR spectra (see below).

The compounds of general Formula (I) or of general Formula (VI) unexpectedly possess odorous properties, in particular a strong sandalwood note, some of which are good compared to those shown by the known derivatives of the prior art, for example Brahmanol.

In particular, the new alcohols of general Formula (I) and of general Formula (VI) exhibit—in both the initial and subsequent odor—a strong, radiant, attractive, natural woody, sandalwood note. They are in particular distinguished by their complex sandalwood odor picture which virtually replicates the multifaceted odor of naturally occurring sandalwood oil. The compounds according to the invention accordingly have an organoleptically highly valuable, intense, natural sandalwood note combined with a surprisingly elevated tenacity.

Compounds with a $R_2$ functionality other than a —H at their C2 position achieve a typical sandalwood, woody fragrance. Thus, the C2 position may preferably have an alkyl group for $R_2$ or may preferably have a substitutent in C2 position, such as —$CH_3$, or a higher straight or branched alkyl chain. However, it was also found that this position may have a C=C double bond giving an alkenyl group or a cyclopropane ring, both of which were found to also work well to give the sandalwood fragrance.

Among of the above-mentioned novel compounds, compounds A, A1, B, B1, I and K having an alkenyl group attached to the butyl chain in position C2 have the most natural, the strongest sandalwood, woody odor.

Compound J having an alkenyl group attached to the butyl chain in position C4 has also a strong sandalwood odor. In addition, compound I having two alkenyl groups attached to the butyl chain in both position C2 and C4 has revealed to have the most persistent sandalwood, woody odor.

The compounds C, D, E and G having a cyclopropane ring attached to the butyl chain in position C2 or C4 exhibit weaker olfactory properties, their odor belongs however also to the sandalwood, woody family of odors.

Compound L, the cyclopropanated analogon of compound J, exhibits a stronger woody, sandalwood note than compound J.

Compounds M, N and O wherein $R_2$ is a methyl group exhibit a woody, floral and sandalwood or a milky, floral, creamy and sandalwood note. The odor intensity of compounds M, N and O is similar to the odor intensity of the compounds according to the general Formula I.

This superiority appears not only with regard to their intrinsic odor-type characters but also, with regard to their secondary properties, in particular: an elevated (inherent) tenacity, a low odor threshold value, elevated impact (odor intensity), or elevated substantivity.

Tenacity, also known as adsorptive capacity, describes a compound's ability to adhere to a substrate. Substantivity describes the ability of a substance to be adsorbed from a usually aqueous phase onto a substrate or also its ability to remain on a substrate after a washing or rinsing operation. This effect is in particular manifested on substrates such as skin, hair and textile fibres (for example cotton, linen, wool and/or synthetic fibres).

This fact may appear astonishing in view of the similarity which exists among the molecular structures of the novel compounds od the general Formula (I) and those of the prior art. However, the odor of a compound is highly sensitive to structural variations.

As a result, their utilisation is advantageous in terms of the nature of the effect achieved.

Among the above novel compounds specified in Table 1, compounds A, A1, B, B1, I, J, and K are preferred due to having the most natural, the strongest and the most persistent sandalwood odor, superior to any existing synthetic, commercially available materials exhibiting a sandalwood odor.

Compound A is the most preferred fragrance substance due to its properties as shown in Table 3.

TABLE 3

| Substance | ODT* (exp.) (ppm (v/v)) | ODT (exp.) ng/l | ODT (exp.) (−log) |
|---|---|---|---|
| A | 5.37E−04 | 4.34 | 8.36E+00 |
| Brahmanol | 1.73E−02 | 141.22 | 6.85E+00 |

*ODT: Odor detection threshold

In comparison with the commercially available sandalwood fragrance substance Brahmanol, compound A exhibits a substantially lower threshold value by the factor of about 35 and is thus distinguished by its intensity. Hence, lower amounts of the compound are necessary to result in an intense, radiant, attractive, natural woody sandalwood note and lower amounts can be used for perfuming.

The ODT was measured by an olfactometer TO8 and a panel of experts according to standard EN 13725.

Compound (I) is also a most preferred fragrance substance due to its tenacity or substantivity resulting in a longlasting odor effect of over 4 to 5 weeks.

The compounds of general Formula (I) or of general Formula (VI) according to the invention can either be used as individual substances or in mixtures with at least one other known fragrance substance selected from an extensive range of natural and synthetic substances available in a large number of fragrance mixtures and/or in admixture with one or more ingredients or excepients conventionally used in conjunction with odorants in fragrance compositions, for example carrier materials and other auxiliary agents commonly used in the art.

The olfactory properties of the novel compounds according to general Formula (I) harmonise with a multitude of natural or synthetic fragrance substances. Hence, they are widely used in perfume compositions, in particular for generating middle and bottom notes.

In particular, the compounds according to general Formula (I) or to general Formula (VI) harmonise particularly well with all floral notes, and they also harmonise with balsamic, resinous dry-out notes or wood notes.

Thus, it is advantageous to combine a compound according to the present invention with at least one other fragrance substance in order to form a novel fragrance composition or in order to round off and refine the odor of a fragrance substance. Interesting and natural novel and original fragrance notes may be created in this manner.

Hence, the present invention relates to a fragrance composition, comprising at least one compound according to the present invention and at least one further fragrance substance.

The following specified fragrance substances can be used, either as individual substances or in mixtures with at least one, two, three or even more fragrance substances, in a large number of fragrance mixtures, selected from an extensive range of natural and synthetic substances.

Fragrance substances which are advantageously suitable for combining are listed for example in S. Arctander, Perfume and Flavor Materials, volumes I and II, Montclair, N.J. 1969, private publication, and/or in H. Surburg, J. Panten, Common Fragrance and Flavor Materials, $6^{th}$ edition, Wiley-VCH, Weinheim 2016. The following list comprises examples of known odourant substances:

extracts of natural raw materials such as essential oils, concretes, absolutes, resins, resinoids, balsams, tinctures such as for example: ambergris tincture; amyris oil; angelica seed oil; angelica root oil; anise oil; valerian oil; basil oil; tree moss absolute; bay oil; artemisia oil; benzoin resin; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute cedar leaf oil; cedarwood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; pine-needle oil; galbanum oil; galbanum resin; geranium oil; grapefruit oil;

guaiac wood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; Litsea cubeba oil; bay leaf oil; mace oil; marjoram oil; mandarin oil; massoia bark oil; mimosa absolute; ambrette oil; musk tincture; muscatel sage oil; nutmeg oil; myrrh absolute; myrrh oil; myrtle oil; clove leaf oil; clove bud oil; neroli oil; olibanum absolute; olibanum oil; opopanax oil; orange blossom absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike lavender oil; star anise oil; styrax oil; tagetes oil; fir needle oil; tea tree oil; terpentine oil; thyme oil; Tolu balsam; tonka absolute; tuberose absolute; vanilla extract; violet leaf absolute; verbena oil; vetiver oil; juniper berry oil; cognac oil; wormwood oil; wintergreen oil; ylang ylang oil; hyssop oil; civet absolute; cinnamon leaf oil; cinnamon bark oil, and fractions thereof or constituents isolated therefrom;

individual fragrance substances from the group comprising hydrocarbons, such as for example 3-carene; alpha-pinene; beta-pinene; alpha-terpinene; gamma-terpinene; p-cymene; bisabolene; camphene; caryophyllene; cedrene; famesene; limonene; longifolene; myrcene; ocimene; valencene; (E,Z)-1,3,5-undecatriene; styrene; diphenylmethane;

aliphatic alcohols such as for example hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixtures of 3,4,5,6,6-pentamethyl-3,4-hepten-2-ol and 3,5,6,6-tetramethyl-4-methylene-heptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and the acetals thereof such as for example hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; 1-(1-methoxypropoxy)-(E/Z)-3-hexene;

aliphatic ketones and the oximes thereof such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulphur-containing compounds such as for example 3-methylthio-hexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

aliphatic nitriles such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids such as for example (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxyacetate; methyl-3,7-dimethyl-2,6-octadienoate; 4-methyl-2-pentyl-crotonate;

acyclic terpene alcohols such as for example: citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

acyclic terpene aldehydes and ketones such as for example geranial; neral; citronellal; 7-hydroxy-3,7-dimethyloctanal; 7-methoxy-3,7-dimethyloctanal; 2,6,10-trimethyl-9-undecenal; geranyl acetone; and the dimethyl and diethyl acetals of geranial, neral, 7-hydroxy-3,7-dimethyloctanal;

cyclic terpene alcohols such as for example: menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

cyclic terpene aldehydes and ketones such as for example menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methylcedryl ketone);

cyclic alcohols such as for example: 4-tert-butylcyclohexanol; 3,3,5-trimethylcyclohexanol; 3-isocamphylcyclohexanol; 2,6,9-trimethyl-Z2, Z5, E9-cyclododecatrien-1-ol; 2-isobutyl-4-methyltetrahydro-2H-pyran-4-ol;

cycloaliphatic alcohols such as for example alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-

(2,2,3-tri methyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl) hexan-3-ol;

cyclic and cycloaliphatic ethers such as for example: cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodeca-hydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

cyclic and macrocyclic ketones such as for example 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as for example 2,4-dimethyl-3-cyclohexene carbaldehyde; 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as for example 1-(3,3-dimethyl-cyclohexyl)-4-penten-1-one; 2,2-dimethyl-1-(2,4-dimethyl-3-cyclohexene-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl) ketone;

esters of cyclic alcohols such as for example 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic alcohols such as for example 1-cyclohexylethyl crotonate; esters of cycloaliphatic carboxylic acids such as for example allyl-3-cyclohexyl propionate; allylcyclohexyl oxyacetate; cis- and trans-methyl dihydrojasmonate; cis- and trans-methyl jasmonate; methyl-2-hexyl-3-oxocyclopentane carboxylate; ethyl-2-ethyl-6,6-dimethyl-2-cyclohexene carboxylate; ethyl-2,3,6,6-tetramethyl-2-cyclohexene carboxylate; ethyl-2-methyl-1,3-dioxolane 2-acetate;

araliphatic alcohols such as for example benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenyl-ethyl butyrate; cinnamyl acetate; 2-phenoxyethyl isobutyrate; 4-methoxybenzyl acetate; araliphatic ethers such as for example: 2-phenyl ethyl methyl ether; 2-phenyl ethyl isoamyl ether; 2-phenyl ethyl 1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

aromatic and araliphatic aldehydes such as for example: benzaldehyde; phenylacetaldehyde; 3-phenylpropanal; hydratropaldehyde; 4-methylbenz-aldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as for example: acetophenone; 4-methyl-acetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and the esters thereof such as for example: benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenylethyl salicylate; methyl-2,4-dihydroxy-3,6-dimethylbenzoate; ethyl-3-phenyl glycidate; ethyl-3-methyl-3-phenyl glycidate;

nitrogenous aromatic compounds such as for example: 2,4,6-trinitro-1,3-dimethyl-5-tert-butylbenzene; 3,5-dinitro-2,6-dimethyl-4-tert-butyl aceto-phenone; cinnamonitrile; 3-methyl-5-phenyl-2-pentenoic acid nitrile;

3-methyl-5-phenylpentanoic acid nitrile; methyl anthranilate; methyl-N-methyl anthranilate; Schiff bases of methyl anthranilate with 7-hydroxy-3,7-dimethyloctanal, 2-methyl-3-(4-tert-butylphenyl)propanal or 2,4-dimethyl-3-cyclohexene carbaldehyde 6-isopropyl quinoline; 6-isobutyl quinoline; 6-sec-butyl quinoline; 2-(3-phenylpropyl)pyridine; indole; skatole; 2-methoxy-3-isopropylpyrazine; 2-isobutyl-3-methoxypyrazine;

phenols, phenyl ethers and phenyl esters such as for example: estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds such as for example: 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as for example: 1,4-octanolide; 3-methyl-1,4-octanolide; 1,4-nonanolide; 1,4-decanolide; 8-decen-1,4-olide; 1,4-undecanolide; 1,4-dodecan-olide; 1,5-decanolide; 1,5-dodecanolide; 4-methyl-1,4-decanolide; 1,15-penta-decanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin;

and mixtures of the above substances.

In such fragrance compositions, the compounds according to the present invention exhibit a positive action over the entire fragrance chord by distinctly enhancing the sandalwood nature of the composition and offering good tenacity and substantivity.

It goes without saying that it is preferred, albeit not absolutely essential, for a fragrance substance composition according to the invention to comprise an amount of a compound according to the invention which is olfactorily perceptible as a sandalwood odor note. In this case, the positive primary property of the compound according to the invention (also) clearly takes effect. For some applications, however, it may be advantageous to make use of only the positive secondary properties of the compound of general Formula (I) according to the invention, i.e. an elevated (inherent) tenacity, a low odor threshold value, elevated impact (odor intensity), or elevated substantivity.

In fragrance substance compositions, the amount of the compound according to the invention used is preferably 0.0001 to 90% by weight, preferably 0.01 to 70% by weight and particularly preferably 0.1 to 50% by weight, relative to the total amount of the fragrance substance composition.

Fragrance substance compositions which contain the compound according to the invention may be used for perfuming in liquid form, undiluted or diluted with a solvent. Solvents suitable for this purpose are for example ethanol, isopropanol, diethylene glycol monoethyl ether, glycerol, propylene glycol, 1,2-butylene glycol, dipropylene glycol, diethyl phthalate, triethyl citrate, isopropyl myristate, triacetin, vegetable oils, etc.

Moreover, fragrance substance compositions which contain the compound according to the invention may be adsorbed on a carrier which ensures both a fine distribution of the fragrance substances in the product and controlled release on use. Such carriers may be porous inorganic materials such as sodium sulphate, silica gels, zeolites, gypsums, clays, clay granules, aerated concrete etc., or organic materials such as woods, cellulose-based substances, sugars, dextrins (for example maltodextrin), or plastics such as PVC, polyvinyl acetates or polyurethanes.

Fragrance substance compositions which contain the compound according to the invention may also be microencapsulated, spray-dried, be provided as inclusion complexes or as extrusion products (i.e. products according to the invention).

Optionally, the properties of the compositions modified in this way may be further optimised with regard to a more targeted fragrance release by "coating" with suitable materials, for which purpose waxy plastics such as for example polyvinyl alcohol are preferably used. The resultant products are in turn products according to the invention.

The fragrance substance compositions according to the invention may be encapsulated, for example, by coacervation methods with the assistance of capsule materials made for example from polyurethane-type substances or soft gelatine.

Spray-dried fragrance substance compositions may be produced for example by spray-drying an emulsion or dispersion containing the fragrance substance composition, wherein modified starches, proteins, dextrin and vegetable gums may be used as carriers. Inclusion complexes may be produced for example by introducing dispersions of the fragrance substance composition and cyclodextrins or urea derivatives into a suitable solvent, for example water.

Extrusion products may be produced by melting the fragrance substance compositions with a suitable waxy substance and extruding with subsequent solidification, optionally in a suitable solvent, for example isopropanol.

In a second aspect, the invention also relates to a method for preparing a compound of general Formula (I) according to the invention or a mixture of compounds of general Formula (I) according to the invention.

The invention is illustrated by the following reaction schemes. The specific synthetic methods followed for preparing the compounds of the invention are based on the application of conventional discrete reaction steps. The details of these processes are given in the reaction schemes and the description which follow. Reagents or reaction conditions may be modified from those given in the following, the originality of the described process residing in the specific choice of the different reaction steps and the reaction sequence adopted. Any abbreviations carry the meaning common in the art.

All of the possible reaction routes to a compound according to general Formula (I) start from campholenic aldehyde (campholene aldehyde) (Formula (II)) or its cyclopropanated derivative (Formula (III)):

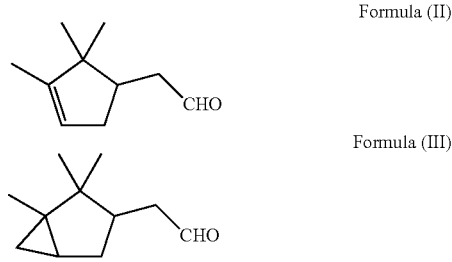

or their enantiomers.

Campholenic aldehyde (Formula (II)) or its cyclopropanated derivative (Formula (III)) is the most important starting material for synthesising the compounds of the present invention, exhibiting the odor profile of sandalwood oil.

The compounds according to Formula (II) and Formula (III) are synthesized according to prior art EP 0 801 049 A2. The compounds according to Formula (II) and (III) have the same basic structure. They merely differ in that compounds of the Formula (II) have an uncyclopropanated cyclopentane ring whereas compounds of the Formula (III) have a cyclopropanated cyclopentane ring. In order to prepare compounds of general Formula (I) having a cyclopropanated cyclopentane ring, compounds of Formula (III) are used as starting material. Consequently, whenever reference is made in the present description to a method for preparing a compound of Formula (I), this is deemed to refer to the compounds of Formula (II) and compounds of Formula (III) similarly.

It is known that campholenic aldehyde can occur in an optically active form or in any mixture of its stereoisomers as a function of the particular isomerism of the alpha-pinene used as the starting material for preparing it. This implies that the compounds derived from campholenic aldehyde can also occur in different stereoisomeric forms.

Consequently, whenever reference is made in the following description to a compound of general Formula (I) as well as Formula (II) and Formula (III), this is deemed to refer to all stereoisomers, in particular to all enantiomers, indifferently to the isomerically pure stereoisomers or mixtures of any of their stereoisomers.

For economic reasons it is preferred to use the compounds as mixtures of their stereoisomers, in particular mixtures of their enantionamers. However, if it is desired to prepare individual stereoisomers, this may be achieved according to methods known in the art, e.g. preparative HPLC, GC, or by departing form chiral starting materials, e.g. starting from enantiomerically pure materials.

Hence, Formula (II) and Formula (III) should encompass both the pure stereoisomers, in particular enantiomers, and mixtures of the stereoisomers, in particular mixtures of the enantiomers. This also implies that the intermediates and compounds obtained from the processes illustrated by the following schemes 1 to 4 can also occur in different isomeric forms, and, thus, should encompass both the pure stereoisomers and mixtures of the stereoisomers.

Preparing Compounds A, B, C or G or their Enantiomers:

In a first variant of the method of the present invention, compounds A, B, C or G are prepared as illustrated in the following reaction scheme 1:

Reaction scheme 1

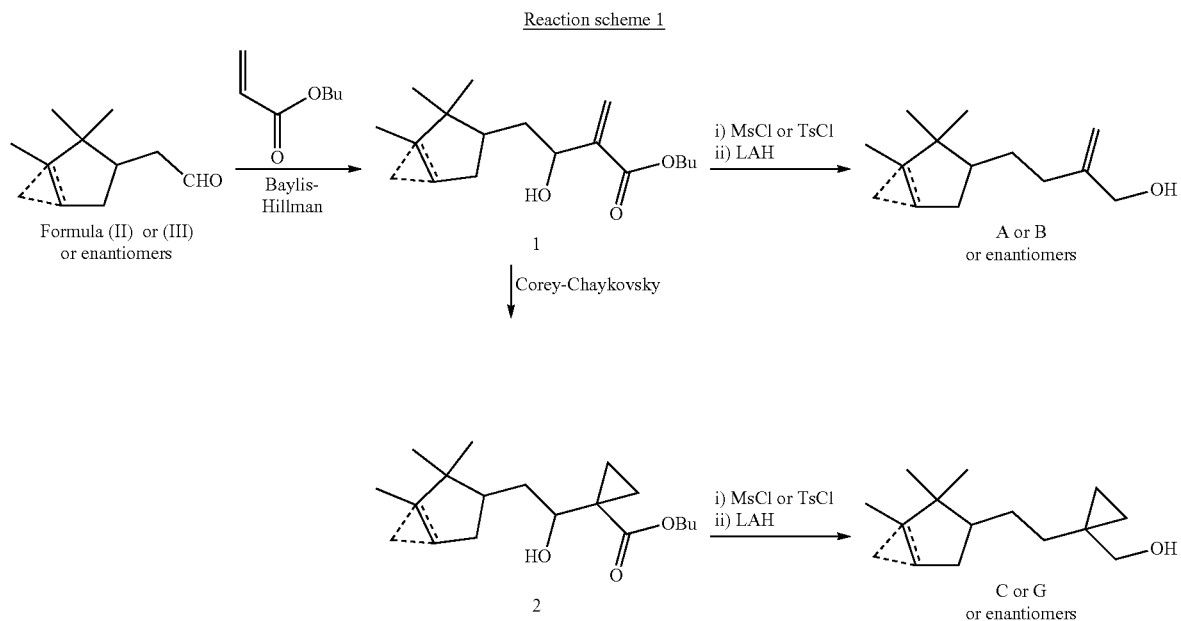

In reaction scheme 1, the campholenic aldehyde of Formula (II) or the cyclopropanated campholenic aldehyde of Formula (III) is converted under Baylis-Hillmann conditions to obtain the intermediate 1. Removal of the hydroxy group using MsCl (methanesulphonyl chloride (mesyl chloride)) or TsCl (tosyl chloride) and TEA (triethylamine), followed by reduction with a reducing agent, preferably LAH (lithium aluminium hydride), gives the allylic alcohol, i.e. compound A or B or their enantiomers.

Alternatively, the intermediate 1 is converted to the intermediate 2 by a Corey-Chaykovsky reaction, which is subsequently mesylated or tosylated and reduced to yield cyclopropanated compound C or G or their enantiomers.

Preparing Compounds D, E, I, J, K or L or their Enantiomers:

In a second variant of the method of the present invention, compounds D, E, I, J, K or L are prepared as illustrated in the following reaction scheme 2:

Reaction scheme 2

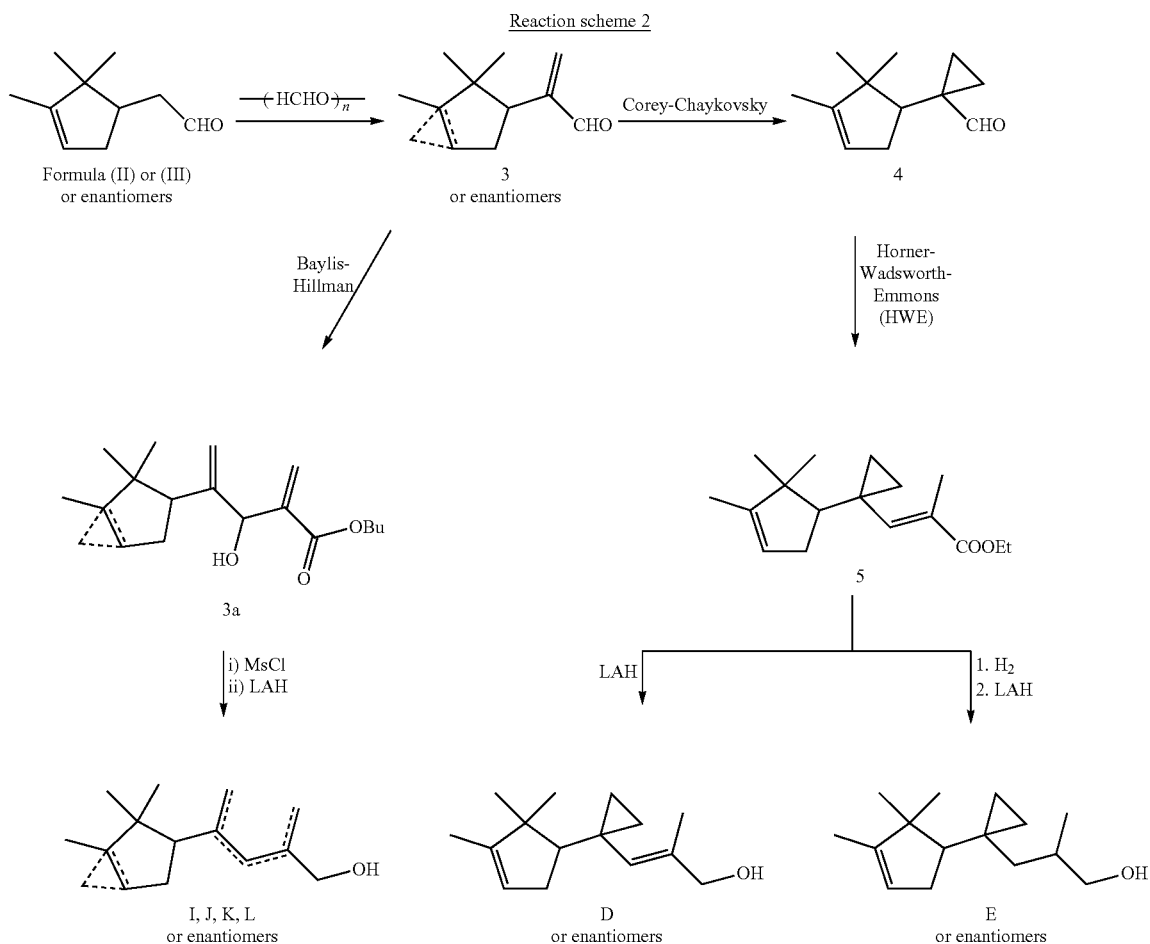

In reaction scheme 2, the campholenic aldehyde of Formula (II) or the cyclopropanated campholenic aldehyde of Formula (III) is reacted with paraformaldehyde, as known in the prior art, to give the α-methylene campholene aldehyde 3. A Baylis-Hillman reaction with the α-methylene campholene aldehyde 3 results in intermediate 3a (uncyclopropanated and cyclopropanated form) which upon mesylation and reduction results in compounds I or J or K or L or their enantiomers, either pure or as a mixture.

Alternatively, selective cyclopropanation of the α-methylene campholene aldehyde 3 under Corey-Chaykovsky conditions gives the cyclopropanated aldehyde 4 in a low-moderate yield, due to the side reaction epoxide formation. A Homer-Wadsworth-Emmons (HWE) reaction of the cyclopropanated aldehyde 4 yields the alkene 5, which upon direct reduction with LAH gives compound D or its enantiomers, or is first selectively hydrogenated using Pd/C and then reduced to give compound E or its enantiomers.

Preparing Compounds A or B or their Enantiomers:

In an alternative method of the present invention, compounds A or B are prepared as illustrated in the following reaction scheme 3:

Reaction scheme 3

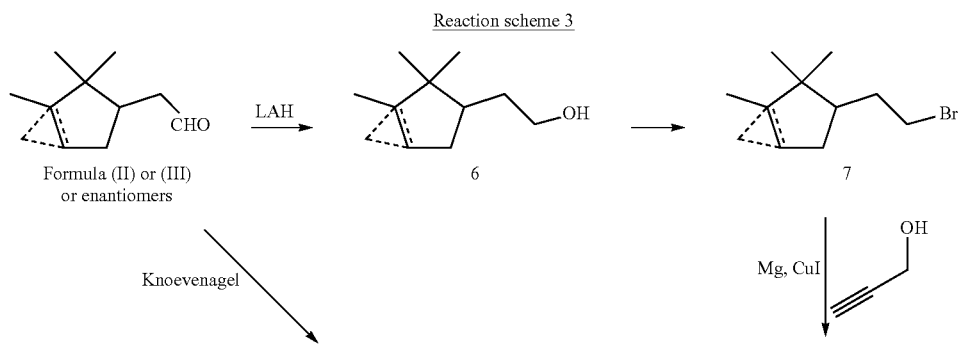

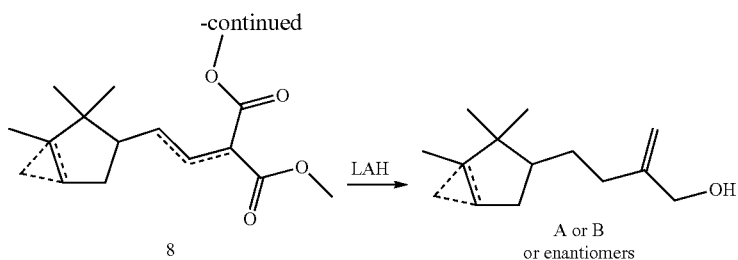

Alternatively, Compound A or B can also be prepared by following the synthetic routes mentioned in reaction scheme 3. A Knoevenagal condensation reaction of the campholenic aldehyde of Formula (II) or the cyclopropanated campholenic aldehyde of Formula (III) using dimethyl malonate gives the dimethyl malonate derivative 8, followed by LAH reduction (Lit.: *JOC*, 1967, 32(1), 113-118; *JACS*, 1977, 99(14), 4778-4782) gives compound A or B or their enantiomers.

The intermediate 8 (uncyclopropanated and cyclopropanated form) in reaction scheme 3 can be used to prepare compound A or B or their enantiomers.

Preparing Compounds A1 or B1 or their Enantiomers:

In another variant of the method of the present invention, compounds A1 or B1 are prepared as illustrated in the following reaction scheme 4:

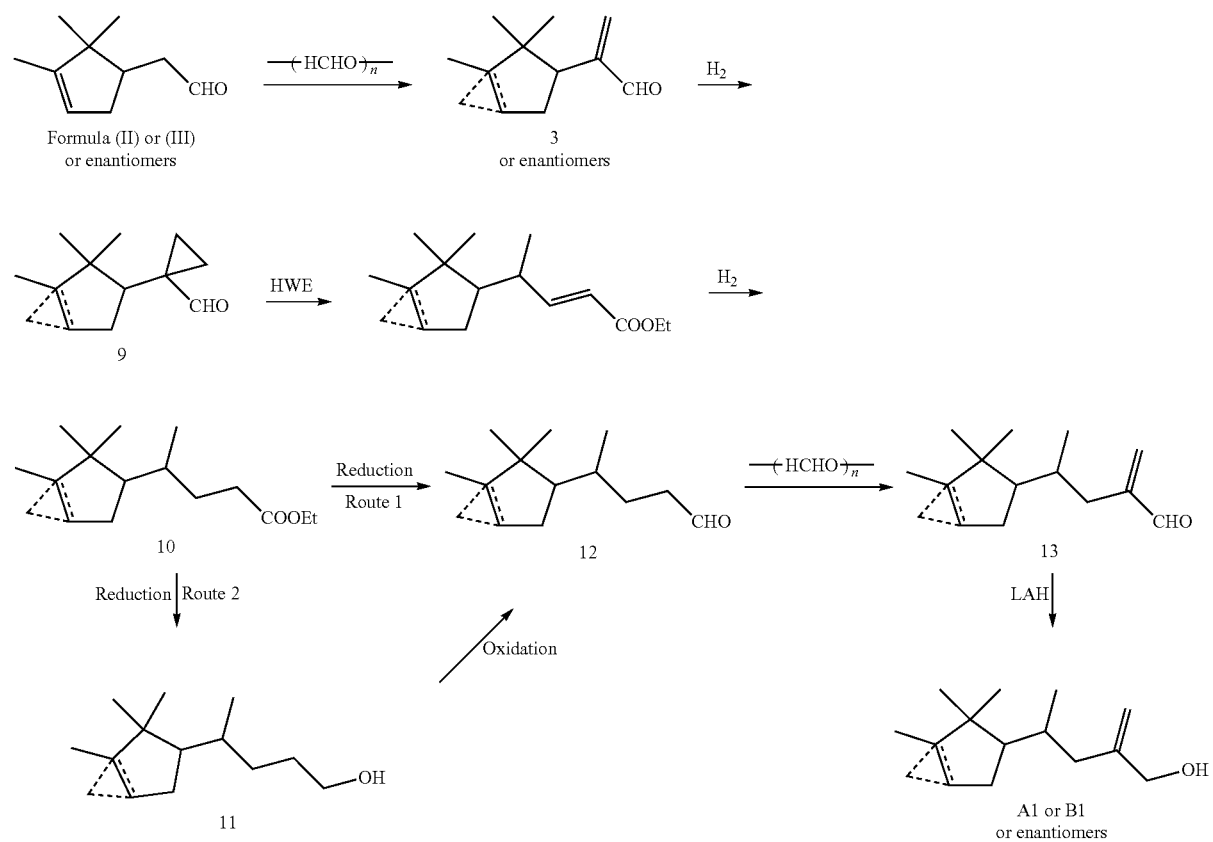

In addition to the above mentioned method, compound A or B can also be synthesised by a sequence of reactions, i.e. reduction of the campholenic aldehyde of Formula (II) or the cyclopropanated campholenic aldehyde of Formula (III) to an alcohol 6, converting the alcohol 6 to the halide 7, which is further reacted with Mg, CuI and propargyl alcohol (WO 2016/074118), resulting in compound A or B or their enantiomers.

In reaction scheme 4, the campholenic aldehyde of Formula (II) or the cyclopropanated campholenic aldehyde of Formula (III) is reacted with paraformaldehyde to give the α-methylene campholene aldehyde 3. The subsequent hydrogenation of the α-methylene campholene aldehyde 3 to intermediate 9, followed by Horner-Wadsworth-Emmons (HWE) and selective hydrogenation using Ra—Ni (room temperature, 2 to 3 bar) gives intermediate 10. The intermediate 10 is further reduced to aldehyde 12 by using DIBAL (diisobutylaluminiumhydrid) or sodium-bis(2-methoxyethoxy)-aluminium (route 1).

Alternatively, intermediate 10 is reduced with LAH to alcohol 11 with 70% yield, which is further oxidized to obtain the aldehyde 12 (route 2).

Aldehyde 12 resulting either from route 1 or route 2 upon condensation reaction with paraformaldehyde afforded the expected intermediate 13 in good yield, followed by reduction with LAH (lithium aluminium hydride) to obtain compound A1 or B1 or their enantiomers.

The compound F is synthesized by an analogous method according to reaction scheme 2.

The compounds of general Formula (VI), in particular the compounds M, N and O, can be prepared in analogy to the method for preparing the compounds of general Formula (I) of the present invention as described above.

The general experimental procedures are as follows.

Baylis-Hillman: In an $N_2$ atmosphere, triethanolamine (28.2 mmol) was slowly added to a mixture of aldehyde (56.3 mmol) and alkene/butyl acrylate (112.6 mmol) at room temperature. DABCO (56.3 mmol) and bismuth triflate (2.8 mmol) was added portionally to this reaction mixture. This reaction mixture was stirred at room temperature for 5 h to 10 days; the number of days varies depending on the target molecule. After complete conversion of the reaction mixture, water was added to the mixture, followed by 2% HCl solution. The resulting compound was extracted using MTBE (3 times). The combined organic layers were washed with saturated $NaHCO_3$ solution and subsequent washed with water several times until the pH of the aqueous layer was neutral. The organic phase was dried with $Na_2SO_4$ and evaporated to obtain the crude product (compound 1, 3a), which upon Kugelrohr distillation gave a yield of 55 to 85% with a purity of >95% (GC).

Mesylation/tosylation: To the product from a Baylis-Hillman reaction, in an $N_2$ atmosphere, a solution of a hydroxy derivative (compound 1 or 3a) (1.0 eq), DMAP (0.2 eq) and triethylamine (1 to 2 eq, depending on the product) in dry THF (5 vol), under stirring, was cooled in an ice-bath. MsCl (methanesulphonyl chloride (mesyl chloride)) or TsCl (tosyl chloride) (1 to 2 eq) was added dropwise to this solution at a temperature of between 0 and 5° C. After the addition of MsCl or TsCl, the reaction was maintained at room temperature until completion of the reaction. Subsequently, water was added to the reaction mixture, and the resulting compound was extracted using MTBE. The combined organic layers were washed with saturated $NaHCO_3$ solution and were washed several times with water until the pH of the aqueous layer was neutral. The organic phase was dried with $Na_2SO_4$ and evaporated to obtain the crude product, which was inputted into the next step (reduction) without further purification.

Reduction: In an $N_2$ atmosphere, the pre-dissolved solution of the mesylated product in THF was added to a mixture of LAH (0.75 to 2.0 eq, depending on the starting material) in THF, at a temperature below 0° C. The reaction was maintained at room temperature until completion of the reaction. The reaction was quenched with ice water, white foam was disrupted using a 25% $H_2SO_4$ solution. The resulting compound was extracted using MTBE. The combined organic layers were washed with water until the pH of the aqueous layer was neutral. The organic phase was dried with $Na_2SO_4$ and evaporated to obtain the crude product, which was either purified by column chromatography (classic or automated) or by distillation (Kugelrohr/Spaltrohr distillation). For complex mixtures, the compound was isolated by a preparative method.

Corey-Chaykovsky: In an $N_2$ atmosphere, DMSO (5 vol) and trimethylsulphoxonium iodide (2.0 eq) was added portionally to a mixture of NaH (2.0 eq) in hexane (6.0 vol). After stirring the reaction mixture at room temperature for about 1 to 2 hours (allowing the formation of sulphur ylide-dimethylsulphonium methylide), an enone (1.0 eq), such as [butyl 3-hydroxy-2-methylene-4-(2,2,3-trimethyl cyclopent-3-en-1-yl)butanoate derivative] was added dropwise. The reaction was maintained at room temperature for 4 to 6 hours until completion of the reaction. After completion of the reaction, water was added to the reaction mixture, and the resulting compound was extracted using MTBE. The combined organic layers were washed with brine and water, dried with $Na_2SO_4$ and subsequently evaporated to obtain the crude product which, upon purification by column chromatography, gave a yield of 15 to 70% and a purity >90% (GC). The yields differ considerably due to the poor selectivity/counter reactive functional group/competitive reaction with other functional group like epoxidation, etc.

Horner-Wadsworth-Emmons: In an $N_2$ atmosphere, triethyl 2-phosphonopropionate or Triethylphosphonoacetate (1.0 eq) was added to a suspension of NaH (50% in mineral oil, 1.5 eq) in THF (5 vol) at a temperature of below 5° C. After stirring for about 45 minutes at room temperature and re-cooling to 0 to 5° C., the corresponding aldehyde (1.0 eq) was added, and the reaction mixture was maintained at room temperature or at reflux until completion of the reaction. After completion of the reaction, the reaction mixture was quenched with ice water (slow addition), and the compound was extracted using MTBE. The combined organic layers were washed with brine and water, dried with $Na_2SO_4$ and evaporated to obtain the crude product which, upon purification by Kugelrohr distillation, followed by column chromatography gave a yield of 70 to 90% and a purity of >90% (GC).

In another aspect, the present invention also relates to a method for producing, enhancing or modifying a sandalwood odor in a formulation, comprising the following steps:
  providing a compound according to the invention or a fragrance composition comprising a compound according to the invention;
  providing a composition of other constituents; and
  mixing the composition of other constituents with an amount of the compound according to the invention or a fragrance composition comprising a compound according to the invention which is sufficient
  (a) to produce a sandalwood odor in the resultant complete mixture; or
  (b) to enhance an existing sandalwood odor in the composition of the other constituents; or
  (c) to modify an existing sandalwood odor in the composition of the other constituents.

Due to its distinguished olfactory properties and secondary properties, which are superior to the sandalwood fragrance substances known from the prior art, a compound according to general Formula (I) or to general Formula (VI) or a fragrance composition comprising a compound according to the invention enables sandalwood notes to be obtained in the resulting perfumed formulations/products that are very clearly reminiscent of sandalwood notes even at a low rate of addition, the overall odorous impression being noticeably harmonious, the radiance being perceptibly increased, and fixation, i.e. the tenacity of the perfume composition, being distinctly enhanced.

In another aspect, the present invention thus relates to the use of a compound according to general Formula (I) or to general Formula (VI) or a fragrance composition comprising a compound according to the invention as an odorant. The comments made above apply correspondingly to preferred compounds and mixtures.

On the basis of their remarkable first olfactory properties and in particular their secondary properties such as tenacity, low odor threshold value, impact (odor intensity) or substantivity the present invention accordingly also relates to the use of a compound according to general Formula (I) or to general Formula (VI) or a fragrance composition comprising at least a compound according to the invention for improving the fixation of a fragrance compound while making simultaneous use of the compound or of the composition containing the compound according to the invention as a fragrance substance and for preparing perfumed products. With regard to the preferred choice of compounds and mixtures according to the invention, the comments made above of course apply correspondingly.

The compounds or compositions which contain a compound according to the invention may be incorporated into products which are perfumed or are intended to be perfumed, in particular formulations serving for personal hygiene such as cleaning agents, laundry agents.

In accordance with a preferred development, the perfumed products according to the invention containing the compound or a fragrance composition which contains a compound according to the invention are produced by incorporating the compound or an composition which contains a compound according to the invention as the substance, without a solvent, as a solution or in the form of a mixture with a solid or liquid carrier and optionally other auxiliaries and/or stabilisers to form a base preparation serving for personal hygiene such as cleaning agents, laundry agents.

The present invention therefore also provides a perfumed product comprising a compound of general Formula (I) or of general Formula (VI) or a fragrance composition which contains at least a compound according to the invention in an effective amount in combination with a carrier or substrate.

Perfumed products according to the invention are for example perfume extracts, eaux de parfum, eaux de toilette, shaving lotions, eaux de cologne, pre-shave products, splash colognes and perfumed tissue wipes, including for perfuming acidic, alkaline and neutral cleaning agents such as for example floor cleaners, window cleaners, dishwashing detergents, bath and sanitary cleaners, scouring creams, solid and liquid toilet cleaners, pulverulent and foam carpet cleaners, textile fresheners, ironing aids, liquid detergents, pulverulent detergents, laundry pre-treatment agents such as bleaches, soaking agents and stain removers, laundry rinse conditioners, laundry soaps, laundry tablets, disinfectants, surface disinfectants as well as air fresheners in liquid or gel form or those applied to a solid carrier, aerosol sprays, waxes and polishes such as furniture polishes, floor waxes and shoe polishes as well as body care products such as for example solid and liquid soaps, shower gels, shampoos, shaving soaps, shaving foams, bath oils, cosmetic emulsions of the oil-in-water, water-in-oil and water-in-oil-in-water type such as for example skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products such as for example hair sprays, hair gels, strengthening hair lotions, hair rinses, permanent and semi-permanent hair dyes, hair styling agents such as cold waving and hair straightening agents, hair tonics, hair creams and lotions, deodorants and antiperspirants such as for example underarm sprays, roll-ons, deodorant sticks, deodorant creams, decorative cosmetic products such as for example eyeshadow, nail varnish, make-up products, lipstick, mascara, as well as candles, lamp oils, incense sticks, insecticides, repellents and fuels or oral and/or dental care products such as toothpastes, tooth gels, tooth powders, mouthwashes, chewing gum and other oral care products.

The products according to the invention may also be semi-finished products comprising a compound of general Formula (I) or of general Formula (VI) or a fragrance composition which contains at least a compound according to the invention in an effective amount.

The percentages at which the compound of general Formula (I) or of general Formula (VI) or a fragrance composition which contains at least a compound according to the invention is used may vary within wide limits, ranging from a few parts per thousand in mass market products such as cleaning agents up to a few percent in alcoholic extracts for fine perfumery. However, even small amounts of the novel compounds or a fragrance composition which contains at least a compound according to the invention provide a rich sandalwood or woody or creamy note and an increased volume and substantivity of a perfumed formulation/product. Preferably, the compound of general Formula (I) or of general Formula (VI) or a fragrance composition which contains at least a compound according to the invention is used in an amount of 0.0001 to 90% by weight, preferably 0.01 to 70% by weight and particularly preferably 0.1 to 50% by weight, based on the total weight of the final formulation.

In yet another aspect, the present invention relates to a compound according to general Formula (IV):

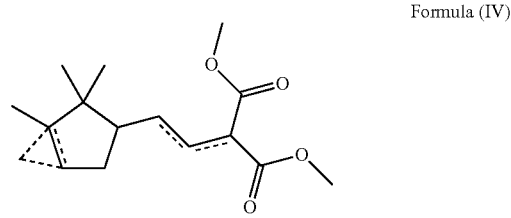

Formula (IV)

wherein the dotted lines represent either a C=C double bond in the butyl chain and/or a C=C double bond or a cyclopropane ring in the cyclopentane ring; or its stereoisomers, in particular its enantiomers.

In a preferred variant, the cyclopentane ring has a C=C double bond in position C3/C4 of the cyclopentane ring, as depicted by the dotted lines in Formula (IV).

In a further preferred variant, in Formula (IV) the cyclopentane ring is monocyclopropanated, as depicted by the dotted lines. In this case, there is preferably a cyclopropane ring formed with two corners from the C atoms in position C3/C4 of the cyclopentane ring.

In yet a further aspect, the present invention relates to a method for preparing a compound of general Formula (IV). Compound of general Formula (IV) can be prepared by following the synthetic routes mentioned in reaction scheme 3. A Knoevenagal condensation reaction of the campholenic aldehyde of Formula (II) or cyclopropanated campholenic aldehyde of Formula (III) using dimethyl malonate gives the compound of general Formula (IV).

In yet further aspect, the present invention relates to the use of compound of general Formula (IV) for preparing compound A or B or their enantiomers.

In yet another aspect, the present invention relates to a compound according to general Formula (V):

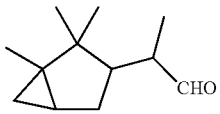

Formula (V)

or its stereoisomers, in particular its enantiomers.

In yet a further aspect, the present invention relates to a method for preparing a compound of general Formula (V). The compound of general Formula (V) can be prepared by following the synthetic routes mentioned in reaction scheme 4: The cyclopropanated campholenic aldehyde of Formula (III) is reacted with paraformaldehyde to give the α-methylene campholene aldehyde 3. The subsequent hydrogenation of the α-methylene campholene aldehyde 3 gives the compound according to general Formula (V).

EXAMPLES

Experimental Data

The following compounds were prepared according to one of the methods of the present invention and described above. The structure determination by means of spectroscopy, was carried out by known techniques.

Butyl-3-hydroxy-2-methylene-4-(2,2,3-trimethylcyclopent-3-en-1-yl) butanoate (1; Campholene Aldehyde Derivative)

$^1$H-NMR (400 MHz, chloroform-d) 6.22 (d, J=1.2 Hz, 1H), 6.21 (d, J=1.2 Hz, 1H), 5.83 (t, J=1.2 Hz, 1H), 5.76 (t, J=1.1 Hz, 1H), 5.24 (dd, J=3.2, 1.6 Hz, 1H), 5.25-5.20 (m, 1H), 4.47-4.42 (m, 1H), 4.39 (dd, J=7.4, 5.7 Hz, 1H), 4.25-4.14 (m, 4H), 2.40 (dddt, J=15.1, 7.7, 2.9, 1.5 Hz, 1H), 2.31 (dddd, J=16.8, 7.0, 2.9, 1.5 Hz, 1H), 2.09 (dddd, J=11.7, 9.6, 7.7, 3.2 Hz, 1H), 1.98-1.81 (m, 2H), 1.75-1.63 (m, 7H), 1.60 (ddt, J=6.2, 4.9, 2.5 Hz, 8H), 1.48-1.36 (m, 4H), 0.99 (s, 3H), 0.95 (t, J=7.5 Hz, 6H), 0.94 (t, J=7.4 Hz, 3H), 0.77 (s, 3H), 0.75 (s, 3H).
$^{13}$C-NMR (101 MHz, chloroform-d) δ 166.70, 166.67, 148.62, 148.44, 143.64, 142.10, 125.31, 124.30, 121.77, 121.56, 72.65, 70.53, 64.71, 64.69, 47.43, 47.00, 46.73, 46.21, 37.03, 36.82, 35.83, 35.09, 30.62, 25.56, 25.51, 19.83, 19.66, 19.24, 19.22, 13.70, 12.64, 12.59.

2-methylene-4-(2,2,3-trimethylcyclopent-3-en-1-yl)butan-1-ol (A)

$^1$H-NMR (400 MHz, chloroform-d) δ 5.23 (dt, J=3.3, 1.6 Hz, 1H), 5.03 (qt, J=1.6, 0.7 Hz, 1H), 4.90 (h, J=1.3 Hz, 1H), 4.10 (t, J=1.2 Hz, 2H), 2.31 (dddt, J=14.4, 6.9, 2.7, 1.4 Hz, 1H), 2.21-2.11 (m, 1H), 2.05-1.95 (m, 1H), 1.87-1.78 (m, 1H), 1.78-1.69 (m, 1H), 1.66-1.57 (m, 1H), 1.60 (dd, J=2.6, 1.6 Hz, 3H), 1.55-1.46 (m, 1H), 1.39 (dtd, J=12.9, 10.6, 4.9 Hz, 1H), 0.98 (s, 3H), 0.77 (s, 3H).

$^{13}$C-NMR (101 MHz, chloroform-d) δ 149.50, 148.76, 121.60, 109.01, 66.00, 50.06, 46.80, 35.52, 32.10, 28.18, 25.84, 19.75, 12.62.
Odor: sandalwood, woody Benzyl-3-hydroxy-2-methylene-4-(1,2,2-trimethyl-3-bicyclo[3.1.0]hexanyl)butanoate (1; Cyclopropanated Campholene Aldehyde Derivative)

$^1$H-NMR (400 MHz, CDCl$_3$) δ 6.20 (d, J=1.2 Hz, 1H), 6.19 (d, J=1.2 Hz, 1H), 5.78 (t, J=1.2 Hz, 1H), 5.72 (t, J=1.1 Hz, 1H), 4.36-4.27 (m, 2H), 4.18 (tt, J=6.6, 1.7 Hz, 4H), 1.87 (dd, J=11.4, 6.1 Hz, 1H), 1.78 (dd, J=12.1, 6.9 Hz, 1H), 1.75-1.71 (m, 1H), 1.67 (ddt, J=8.8, 7.9, 5.6 Hz, 4H), 1.54 (ddd, J=12.2, 9.6, 2.6 Hz, 1H), 1.50-1.38 (m, 8H), 1.38-1.28 (m, 1H), 1.12-1.06 (m, 1H), 1.05 (s, 3H), 1.03 (s, 3H), 0.99 (q, J=4.2 Hz, 2H), 0.96 (td, J=7.4, 1.1 Hz, 6H), 0.89 (s, 3H), 0.87 (s, 3H), 0.78 (s, 3H), 0.75 (s, 3H), 0.50 (dd, J=4.7, 3.5 Hz, 1H), 0.38 (dd, J=4.7, 3.6 Hz, 1H), 0.06-0.02 (m, 2H).
$^{13}$C-NMR (101 MHz, CDCl$_3$) δ 166.65, 143.64, 142.16, 125.18, 124.26, 72.45, 70.47, 64.72, 64.68, 41.59, 41.34, 41.33, 40.08, 37.34, 36.99, 32.68, 31.83, 31.32, 31.04, 30.62, 30.60, 22.78, 22.73, 22.60, 19.85, 19.73, 19.24, 19.22, 17.45, 17.38, 14.00, 13.92, 13.69.

2-methylene-4-(1,2,2-trimethyl-3-bicyclo[3.1.0]hexanyl)butan-1-ol (B)

$^1$H-NMR (600 MHz, CDCl$_3$) δ 5.00 (d, J=1.3 Hz, 1H), 5.75 (t, J=1.4 Hz, 1H), 4.13 (m, 2H), 2.19 (m, 1H), 2.01 (m, 1H), 1.89 (dd, J=10.9, 6.4 Hz, 1H), 1.81 (dd, J=12.4, 7.1 Hz, 1H), 1.81 (dd, J=11.1, 6.7 Hz, 1H), 1.74 (m, 1H), 1.32 (m, 1H), 1.05 (m, 1H), 1.03 (s, 3H), 0.97 (q, J=4.21, 1H) 0.50 (dd, J=4.5, 3.1 Hz, 1H), 0.38 (dd, J=4.2, 3.3 Hz, 1H), 0.83 (s, 3H), 0.78 (s, 3H),
$^{13}$C-NMR (151 MHz, CDCl$_3$) δ 150.23, 138.56, 63.84, 66.31, 37.62, 32.57, 30.59, 29.43, 23.46, 17.98, 19.86, 21.91, 14.06, 13.71.
Odor: sandalwood, woody, creamy Dimethyl-2-[2-(2,2,3-trimethylcyclopent-3-en-1-yl) ethylidene]propanedioate, dimethyl 2-[-2-(2,2,3-trimethylcyclopent-3-en-1-yl)vinyl]propanedioate (8)

$^1$H-NMR (400 MHz, CDCl$_3$) δ 7.09 (t, J=7.9 Hz, 1H), 5.75 (dd, J=15.2, 7.4 Hz, 1H), 5.69 (dd, J=15.4, 7.7 Hz, 1H), 5.22 (qd, J=2.8, 1.9, 1.4 Hz, 2H), 4.07 (d, J=7.9 Hz, 1H), 3.83 (s, 3H), 3.78 (s, 3H), 3.75 (s, 3H), 3.75 (s, 3H), 2.44 (ddd, J=14.1, 7.7, 4.2 Hz, 2H), 2.36-2.18 (m, 2H), 2.12 (ddp, J=16.0, 9.3, 2.5 Hz, 1H), 1.98-1.89 (m, 2H), 1.92-1.84 (m, 1H), 1.61 (dd, J=2.5, 1.5 Hz, 6H), 1.00 (s, 3H), 0.98 (s, 3H), 0.79 (s, 3H), 0.74 (s, 3H).
$^{13}$C-NMR (101 MHz, CDCl$_3$) δ 168.87, 168.83, 166.00, 164.39, 150.37, 148.20, 147.93, 138.07, 128.05, 121.62, 121.46, 121.30, 55.39, 53.69, 52.67, 52.67, 52.33, 52.21, 49.48, 48.39, 47.03, 35.24, 34.93, 30.68, 25.73, 25.40, 20.45, 19.71, 12.63, 12.61.

Butyl-1-[1-hydroxy-2-(2,2,3-trimethylcyclopent-3-en-1-yl)ethyl]cyclopropanecarboxylate (2; Campholene Aldehyde Derivative)

$^1$H-NMR (400 MHz, CDCl$_3$) δ 5.26-5.23 (m, 1H), 4.09 (qq, J=8.2, 4.2 Hz, 2H), 3.20-3.06 (m$_c$, 1H), 2.35 (m$_c$, 1H), 2.15-2.02 (m, 1H), 2.00-1.79 (m, 1H), 1.79-1.63 (m, 2H), 1.61 (m$_c$, 5H), 1.50-1.27 (m$_c$, 2H), 1.18 (dddd, J=19.3, 9.6, 6.8, 4.1 Hz, 2H), 1.00 (q, J=3.3 Hz, 2H), 0.99 (s, 3H), 0.94 (td, J=7.2, 1.8 Hz, 3H), 0.75 (s, 3H).

$^{13}$C-NMR (101 MHz, CDCl$_3$) δ 174.53, 148.27, 122.07, 75.97, 64.43, 48.21, 47.11, 36.69, 35.94, 30.59, 28.36, 25.75, 19.55, 19.20, 14.95, 13.67, 12.81, 12.61.

[1-[2-(2,2,3-trimethylcyclopent-3-en-1-yl)ethyl]cyclopropyl]methanol (G)

$^1$H-NMR (600 MHz, C$_6$D$_6$)) δ 5.28 (hept, J=1.6 Hz, 1H), 3.25 (d, J=11.2 Hz, 1H), 3.20 (d, J=11.2 Hz, 1H), 2.31 (dddt, J=15.2, 7.6, 3.0, 1.6 Hz, 1H), 1.84 (dddd, J=17.8, 9.6, 4.8, 2.5 Hz, 1H), 1.75 (dddd, J=11.2, 9.6, 7.6, 3.8 Hz, 1H), 1.63-1.55 (m, 1H), 1.58 (dt, J=2.9, 1.6 Hz, 3H), 1.46 (ddd, J=13.4, 12.0, 4.0 Hz, 1H), 1.38-1.30 (m, 1H), 1.25 (ddd, J=13.4, 11.6, 4.8 Hz, 1H), 0.98 (s, 3H), 0.80 (s, 3H), 0.60 (s, 1H), 0.24-0.16 (m, 4H).

$^{13}$C-NMR (151 MHz, C$_6$D$_6$) δ 148.60, 122.22, 68.04, 51.01, 47.07, 36.22, 33.72, 27.31, 26.14, 22.71, 19.94, 12.80, 10.20, 10.09.

Odor: sandalwood, woody, creamy, sweet, soft

Butyl-1-[1-hydroxy-2-(1,2,2-trimethyl-3-bicyclo [3.1.0]hexanyl)ethyl]cyclopropane carboxylate (2; Cyclopropanated Campholene Aldehyde Derivative)

$^1$H-NMR (400 MHz, CDCl$_3$) δ 4.17-4.01 (m, 4H), 3.12-3.02 (m, 1H), 3.02-2.92 (m, 1H), 1.87-1.76 (m, 2H), 1.69 (ddt, J=13.7, 8.5, 2.9 Hz, 2H), 1.64-1.54 (m, 4H), 1.47 (tdd, J=11.8, 5.5, 2.4 Hz, 2H), 1.43-1.27 (m, 5H), 1.26 (s, 3H), 1.23-1.10 (m, 3H), 1.04 (s, 3H), 1.03 (s, 3H), 1.00-0.96 (m, 2H), 0.96-0.91 (m, 6H), 0.90 (s, 3H), 0.88 (d, J=2.7 Hz, 3H), 0.76 (s, 3H), 0.74 (s, 3H), 0.69 (ddd, J=9.3, 6.8, 4.2 Hz, 3H), 0.50 (t, J=4.2 Hz, 1H), 0.43 (t, J=4.1 Hz, 1H), 0.04-0.02 (m, 2H).

$^{13}$C-NMR (101 MHz, CDCl$_3$) δ 202.83, 174.72, 174.47, 75.86, 74.21, 64.43, 42.01, 41.68, 41.23, 39.90, 36.08, 35.73, 33.45, 31.85, 31.39, 31.01, 30.60, 30.58, 28.80, 28.36, 22.98, 22.79, 22.56, 22.54, 19.88, 19.60, 19.23, 19.20, 17.46, 17.39, 15.83, 14.90, 14.02, 13.89, 13.67, 12.74.

[1-[2-(1,2,2-trimethyl-3-bicyclo[3.1.0]hexanyl)ethyl] cyclopropyl]methanol (C)

$^1$H-NMR (400 MHz, CDCl$_3$) δ 3.40 (d, J=3.0 Hz, 2H), 1.75-1.69 (m, 1H), 1.39 (d, J=7.0 Hz, 2H), 1.36-1.17 (m, 2H), 1.10-1.01 (m, 5H), 1.00-0.96 (m, 2H), 0.96-0.82 (m, 4H), 0.80-0.73 (m, 3H), 0.46-0.28 (m, 4H), 0.01 (qt, J=7.6, 3.5 Hz, 1H).

$^{13}$C-NMR (101 MHz, CDCl$_3$) δ 68.54, 44.50, 41.39, 33.32, 32.53, 31.50, 26.39, 23.04, 22.71, 22.58, 19.78, 17.42, 13.98, 10.10, 9.97.

Odor: sandalwood, woody, creamy 2-methylene-4-(2,2,3-trimethylcyclopent-3-en-1-yl) pent-4-en-1-ol; (2E)-2-methyl-4-(2,2,3-trimethylcyclopent-3-en-1-yl)penta-2,4-dien-1-ol; (E)-2-methylene-4-(2,2,3-trimethylcyclopent-3-en-1-yl)pent-3-en-1-ol (I, J, K)

$^1$H-NMR (400 MHz, CDCl$_3$) δ 5.92 (p, J=1.6 Hz, 1H), 5.31-5.18 (m, 5H), 5.13 (dd, J=2.3, 1.2 Hz, 1H), 5.04 (ddp, J=9.1, 6.5, 1.3 Hz, 2H), 4.96 (q, J=2.5, 1.8 Hz, 1H), 4.08 (s, 2H), 3.40-3.25 (m, 2H), 2.62-2.50 (m, 2H), 2.39-2.19 (m, 3H), 1.84 (d, J=1.5 Hz, 3H), 1.72 (dd, J=2.6, 1.3 Hz, 5H), 1.60 (td, J=3.4, 2.6, 1.6 Hz, 10H), 1.58-1.51 (m, 4H), 1.18 (dd, J=6.9, 4.4 Hz, 6H), 1.05 (s, 2H), 1.03 (s, 6H), 0.77 (s, 3H), 0.72 (s, 4H).

$^{13}$C-NMR (101 MHz, CDCl$_3$) δ 201.43, 201.35, 147.61, 145.56, 135.98, 127.72, 122.39, 122.31, 121.59, 121.50, 121.34, 114.83, 69.09, 59.09, 57.10, 46.46, 46.40, 33.39, 33.21, 26.92, 26.59, 21.14, 20.77, 17.19, 15.56, 14.27, 14.09, 12.74.

Odor: sandalwood, creamy, woody 2-methyl-4-(1,2,2-trimethyl-3-bicyclo[3.1.0]hexanyl)penta-2,4-dien-1-ol (L; One of its Isomers)

$^1$H-NMR (600 MHz, chloroform-d) δ 5.82 (t, J=1.6 Hz, 1H), 4.99 (t, J=1.8 Hz, 1H), 4.93 (d, J=1.8 Hz, 1H), 4.11-4.05 (m, 2H), 2.01-1.92 (m, 1H), 1.90 (dd, J=11.8, 6.0 Hz, 1H), 1.81 (d, J=1.5 Hz, 3H), 1.78-1.72 (m, 1H), 1.67-1.61 (m, 1H), 1.03 (s, 3H), 0.95 (s, 3H), 0.70 (s, 3H), 0.51-0.47 (m, 1H), 0.05-0.03 (m, 1H).

$^{13}$C-NMR (151 MHz, chloroform-d) δ 144.66, 135.60, 128.34, 114.76, 69.00, 50.32, 42.13, 30.84, 29.67, 23.59, 21.95, 20.80, 17.34, 15.53, 13.89.

Odor: sandalwood, woody, creamy

Ethyl-2-methyl-3-[1-(2,2,3-trimethylcyclopent-3-en-1-yl)cyclopropyl]prop-2-enoate (5)

$^1$H-NMR (400 MHz, CDCl$_3$) δ 7.03 (d, J=1.6 Hz, 1H), 5.17 (p, J=2.0 Hz, 1H), 4.18 (q, J=7.1 Hz, 2H), 2.12-2.00 (m, 2H), 1.93 (d, J=1.4 Hz, 3H), 1.85-1.75 (m, 1H), 1.61-1.53 (m, 3H), 1.28 (t, J=7.1 Hz, 3H), 1.03 (s, 3H), 0.98 (s, 3H), 0.85-0.66 (m, 2H), 0.66-0.57 (m, 1H), 0.57-0.47 (m, 1H).

$^{13}$C-NMR (101 MHz, CDCl$_3$) δ 168.78, 148.21, 145.75, 129.86, 120.65, 60.43, 56.06, 48.51, 31.79, 27.36, 21.87, 19.84, 14.29, 13.87, 12.44, 11.82, 11.73.

2-methyl-3-[1-(2,2,3-trimethylcyclopent-3-en-1-yl) cyclopropyl]prop-2-en-1-ol (D)

$^1$H-NMR (400 MHz, CDCl$_3$) δ 5.75-5.71 (m, 1H), 5.64 (s, 1H), 5.17 (dt, J=2.8, 1.7 Hz, 2H), 4.36-4.25 (m, 2H), 3.97 (d, J=1.2 Hz, 2H), 2.01 (dd, J=7.2, 5.6 Hz, 3H), 1.95-1.88 (m, 1H), 1.87-1.79 (m, 2H), 1.77 (d, J=1.4 Hz, 3H), 1.76 (d, J=1.5 Hz, 3H), 1.54 (dq, J=3.5, 1.7 Hz, 6H), 1.05 (s, 6H), 0.97 (s, 3H), 0.96 (s, 3H), 0.70-0.61 (m, 4H), 0.53-0.45 (m, 2H), 0.43-0.36 (m, 2H).

$^{13}$C-NMR (101 MHz, CDCl$_3$) δ 171.18, 148.23, 148.21, 137.32, 136.54, 133.05, 130.84, 120.79, 120.66, 69.10, 62.52, 60.41, 57.31, 56.25, 48.63, 48.57, 31.98, 27.60, 21.96, 21.94, 21.05, 20.44, 18.87, 18.80, 15.09, 14.20, 12.43, 12.41, 11.76, 11.73, 11.64.

Odor: sandalwood, woody, amber like 2-methyl-3-[1-(2,2,3-trimethylcyclopent-3-en-1-yl) cyclopropyl]propan-1-ol (E)

$^1$H-NMR (600 MHz, benzene-d6) δ 5.18-5.15 (m, 1H), 3.16 (qd, J=10.2, 6.1 Hz, 2H), 2.39 (dd, J=10.5, 8.3 Hz, 1H), 2.24 (ddd, J=14.2, 3.5, 1.9 Hz, 1H), 1.92 (dhd, J=11.0, 6.5, 3.8 Hz, 1H), 1.86-1.79 (m, 1H), 1.55 (ddp, J=14.4, 10.2, 2.3 Hz, 1H), 1.55-1.53 (m, 3H), 1.18 (s, 3H), 1.02 (s, 3H), 0.90 (d, J=6.7 Hz, 3H), 0.58 (dt, J=8.1, 4.3 Hz, 1H), 0.38-0.33 (m, 1H), 0.23 (dd, J=14.2, 11.3 Hz, 1H), 0.16 (dt, J=8.7, 4.3 Hz, 1H), 0.13 (ddd, J=9.1, 4.8, 3.7 Hz, 1H).

$^{13}$C-NMR (151 MHz, benzene-d6) δ 148.4, 121.3, 69.2, 49.3, 48.9, 41.4, 33.5, 32.2, 28.2, 21.4, 17.0, 16.5, 12.7, 10.7, 8.9.

Odor: sandalwood, woody (4-[1-(2,2,3-trimethylcyclopent-3-en-1-yl)cyclopropyl]but-3-en-2-ol (F)

¹H-NMR (400 MHz, CDCl₃) δ 5.99 (ddd, J=15.5, 2.1, 1.1 Hz, 2H), 5.29 (ddd, J=15.5, 6.9, 2.8 Hz, 2H), 5.19 (tq, J=3.2, 1.6 Hz, 2H), 4.24 (p, J=6.5 Hz, 2H), 2.22 (dddq, J=14.3, 10.1, 6.3, 2.2 Hz, 2H), 2.06-1.94 (m, 2H), 1.74-1.63 (m, 2H), 1.56 (q, J=1.9 Hz, 6H), 1.38 (t, J=3.2 Hz, 2H), 1.22 (dd, J=6.3, 2.7 Hz, 6H), 1.01 (d, J=1.6 Hz, 6H), 0.98-0.95 (m, 6H), 0.64-0.51 (m, 8H).

¹³C-NMR (101 MHz, CDCl₃) δ 148.05, 148.03, 135.64, 135.49, 129.91, 129.84, 121.05, 121.04, 69.13, 56.20, 55.94, 48.66, 32.88, 32.78, 28.27, 28.17, 23.36, 22.40, 22.37, 21.58, 21.56, 13.05, 13.02, 12.89, 12.48, 12.41.

Odor: creamy, chocolate, natural character of patchouli

1-[1-(hydroxymethyl)cyclopropyl]-2-(2,2,3-trimethylcyclopent-3-en-1-yl) ethanol

¹H-NMR (400 MHz, CDCl₃) δ 5.26-5.23 (m, 1H), 5.22 (dt, J=3.2, 1.8 Hz, 1H), 4.09 (qq, J=8.2, 4.2 Hz, 4H), 3.20-3.06 (m, 2H), 2.82 (d, J=22.5 Hz, 2H), 2.35 (ddddt, J=13.5, 7.9, 6.5, 3.0, 1.5 Hz, 2H), 2.15-2.02 (m, 1H), 2.00-1.79 (m, 4H), 1.79-1.63 (m, 3H), 1.61 (tq, J=5.4, 1.6 Hz, 10H), 1.50-1.27 (m, 4H), 1.18 (dddd, J=19.3, 9.6, 6.8, 4.1 Hz, 2H), 1.00 (q, J=3.3 Hz, 1H), 0.99 (s, 3H), 0.97 (2, 3H), 0.94 (td, J=7.2, 1.8 Hz, 6H), 0.84-0.79 (m, 2H), 0.76 (s, 3H), 0.75 (s, 3H).

¹³C-NMR (101 MHz, CDCl₃) δ 174.77, 174.53, 148.73, 148.27, 122.07, 121.42, 75.97, 74.10, 64.44, 64.43, 48.21, 47.11, 46.60, 46.00, 36.69, 35.94, 35.31, 35.10, 30.61, 30.59, 28.81, 28.36, 25.75, 25.49, 19.90, 19.55, 19.24, 19.20, 15.69, 14.95, 13.67, 12.81, 12.77, 12.64, 12.61.

2-(2,2,3-trimethylcyclopent-3-en-1-yl)prop-2-enal (Lit.: Chem. Biodiversity 2008, 5, 1000-1010) (3; Campholene Aldehyde Derivative)

¹H NMR (600 MHz, CDCl₃) δ 9.58 (s, 1H), 6.35 (s, 1H), 6.12 (s, 1H), 5.30 (h, J=1.8 Hz, 1H), 3.21 (d, J=8.2 Hz, 1H), 2.37-2.31 (m, 2H), 1.61 (q, J=2.0 Hz, 3H), 1.04 (s, 3H), 0.69 (s, 3H).

¹³C NMR (151 MHz, CDCl₃) δ 195.29, 151.29, 147.30, 135.61, 121.41, 48.14, 46.42, 34.64, 26.46, 21.66, 12.78.

2-(2,2,3-trimethylcyclopent-3-en-1-yl)propanal (9; Campholene Aldehyde Derivative)

¹H NMR (600 MHz, C₆D₆) δ 9.39 (d, J=3.0 Hz, 1H), 5.08 (dp, J=3.4, 1.7 Hz, 1H), 2.24-2.18 (m, 1H), 2.16 (dddd, J=12.4, 6.2, 3.2, 1.7 Hz, 1H), 1.89 (ddtd, J=13.8, 9.5, 4.8, 2.4 Hz, 1H), 1.70 (td, J=8.8, 7.8 Hz, 1H), 1.44 (dq, J=3.1, 1.6 Hz, 3H), 0.89 (s, 3H), 0.87 (d, J=6.9 Hz, 3H), 0.71 (s, 3H).

¹³C NMR (151 MHz, C₆D₆) δ 203.90, 148.04, 121.92, 51.87, 48.09, 47.95, 33.71, 27.09, 20.35, 13.84, 12.58.

2-(1,2,2-trimethyl-3-bicyclo[3.1.0]hexanyl) propanal (9; Cyclopropanated Campholene Aldehyde Derivative)

¹H NMR (600 MHz, C₆D₆) δ 9.26 (d, J=3.4 Hz, 1H), 9.23 (d, J=4.6 Hz, 1H), 2.06-1.99 (m, 1H), 1.95 (dqd, J=10.1, 6.8, 3.4 Hz, 1H), 1.63 (dd, J=12.2, 6.9 Hz, 1H), 1.51-1.44 (m, 1H), 1.38 (ddd, J=12.3, 11.5, 4.3 Hz, 1H), 1.24-1.20 (m, 2H), 1.08-1.01 (m, 1H), 0.89 (s, 6H), 0.87 (s, 3H), 0.85-0.81 (m, 2H), 0.83 (s, 3H), 0.79 (d, J=6.8 Hz, 3H), 0.77 (s, 3H), 0.67 (s, 3H), 0.64 (d, J=6.8 Hz, 3H), 0.34 (dd, J=4.9, 3.5 Hz, 1H), 0.29 (t, J=5.0, 4.0 Hz, 1H), −0.04 (dd, J=7.9, 4.9 Hz, 1H), −0.07 (ddd, J=7.9, 4.9, 0.7 Hz, 1H).

¹³C NMR (151 MHz, C₆D₆) δ 203.79, 203.01, 48.25, 48.00, 45.62, 45.44, 41.95, 41.67, 31.95, 31.82, 31.35, 30.46, 24.56, 23.58, 22.82, 22.22, 20.55, 19.77, 17.30, 17.13, 14.16, 14.13, 13.73, 13.31.

Ethyl-4-(2,2,3-trimethylcyclopent-3-en-1-yl)pent-2-enoate

¹H NMR (400 MHz, CDCl₃) δ 6.89 (dd, J=15.6, 9.0 Hz, 1H), 5.77 (dd, J=15.6, 0.9 Hz, 1H), 5.20-5.17 (m, 1H), 4.18 (q, J=7.2 Hz, 2H), 2.51-2.41 (m, 1H), 2.18-2.10 (m, 1H), 1.96-1.81 (m, 1H), 1.79-1.70 (m, 1H), 1.61-1.55 (m, 3H), 1.32-1.24 (m, 3H), 1.14 (d, J=6.6 Hz, 3H), 1.10 (s, 3H), 0.89 (s, 3H).

¹³C NMR (101 MHz, CDCl₃) δ 167.04, 154.28, 148.46, 121.43, 119.33, 60.12, 54.67, 47.17, 38.55, 34.80, 27.29, 19.72, 19.40, 14.29, 12.48.

Ethyl-4-(2,2,3-trimethylcyclopent-3-en-1-yl)pentanoate (10)

¹H NMR (400 MHz, CDCl₃) δ 5.24-5.17 (m, 1H), 4.13 (q, J=7.1, 2.8 Hz, 2H), 2.41-2.31 (m, 1H), 2.31-2.19 (m, 2H), 1.98-1.86 (m, 1H), 1.86-1.78 (m, 1H), 1.70-1.59 (m, 2H), 1.59-1.55 (m, 3H), 1.52-1.29 (m, 1H), 1.26 (t, 3H), 1.08 (s, 3H), 0.99 (d, J=6.1 Hz, 3H), 0.86 (s, 3H).

¹³C NMR (101 MHz, CDCl₃) δ 174.29, 148.82, 121.24, 60.19, 55.43, 46.95, 34.73, 33.92, 31.47, 30.70, 27.32, 19.08, 18.75, 14.26, 12.60.

4-(2,2,3-trimethylcyclopent-3-en-1-yl)pentan-1-ol (11)

¹H NMR (400 MHz, CDCl₃) δ 5.24-5.16 (m, 1H), 3.68-3.58 (m, 2H), 2.29-2.20 (m, 1H), 1.96-1.84 (m, 1H), 1.75-1.59 (m, 3H), 1.58 (s, 3H), 1.53-1.42 (m, 2H), 1.18-1.09 (m, 1H), 1.08 (s, 3H), 1.00 (d, J=6.1 Hz, 3H), 0.86 (s, 3H).

¹³C NMR (101 MHz, CDCl₃) δ 148.93, 121.26, 63.61, 55.61, 46.93, 34.83, 34.16, 31.53, 29.56, 27.36, 27.36, 19.13, 12.61.

2-ethyl-4-(2,2,3-trimethylcyclopent-3-en-1-yl)pent-2-en-1-ol (M)

¹H NMR (600 MHz, C₆D₆) δ 5.24 (dp, J=3.2, 1.6 Hz, 1H), 5.18 (dt, J=10.0, 1.1 Hz, 1H), 3.85 (d, J=1.3 Hz, 2H), 2.59 (tq, J=9.8, 6.6 Hz, 1H), 2.20 (dddq, J=15.7, 8.0, 3.0, 1.5 Hz, 1H), 2.12 (dqd, J=13.8, 7.6, 0.8 Hz, 1H), 2.04 (dqd, J=13.6, 7.5, 0.6 Hz, 1H), 1.89 (ddp, J=15.8, 9.9, 2.6, 1.9 Hz, 1H), 1.69 (td, J=9.8, 8.0 Hz, 1H), 1.55 (dt, J=2.9, 1.6 Hz, 3H), 1.11 (s, 3H), 1.05 (d, J=6.6 Hz, 3H), 0.96 (t, J=7.6 Hz, 3H), 0.91 (s, 3H).

¹³C NMR (151 MHz, C₆D₆) δ 148.63, 138.22, 132.08, 122.13, 66.79, 56.03, 47.01, 35.73, 33.79, 27.64, 21.59, 21.43, 19.47, 13.58, 12.70.

Odor: woody, floral, sandalwood 2-ethyl-4-(2,2,3-trimethylcyclopent-3-en-1-yl)penta-2,4-dien-1-ol and 2-ethylidene-4-(2,2,3-trimethylcyclopent-3-en-1-yl)pent-3-en-1-ol ¹H NMR (600 MHz, C₆D₆) δ 5.97 (s, 1H), 5.27 (m_c, 1H), 5.12 (dd, J=2.4, 1.2 Hz, 1H), 5.06 (t, J=1.9 Hz, 1H), 3.87

($m_c$, 2H), 2.65 (dd, J=9.4, 7.9 Hz, 1H), 2.41 (dddt, J=18.2, 8.3, 4.8, 2.4 Hz, 1H), 2.33 ($m_c$, 1H), 2.29-2.23 (m, 2H), 1.57 (s, 3H), 1.09 (s, 3H), 0.97 (t, J=7.5 Hz, 3H), 0.85 (s, 3H).

$^{13}$C NMR (151 MHz, $C_6D_6$) δ 147.53, 146.14, 142.26, 127.38, 121.88, 113.99, 66.13, 57.67, 48.26, 33.93, 26.79, 22.46, 21.07, 13.46, 12.88.

2-ethylidene-4-(2,2,3-trimethylcyclopent-3-en-1-yl)pent-3-en-1-ol $^1$H NMR (600 MHz, $C_6D_6$) δ 5.88 (dt, J=2.8, 1.4 Hz, 1H), 5.41 (qd, J=7.1, 1.3 Hz, 1H), 5.27 ($m_c$, 1H), 4.07 ($m_c$, 2H), 2.61 (td, J=8.1, 1.0 Hz, 1H), 2.41 (dddt, J=18.2, 8.3, 4.8, 2.4 Hz, 1H), 2.27 ($m_c$, 1H), 1.81 (d, J=1.4 Hz, 3H), 1.57-1.53 (m, 6H), 1.07 (s, 3H), 0.85 (s, 3H).

$^{13}$C NMR (151 MHz, $C_6D_6$) δ 147.20, 138.97, 138.08, 127.88, 125.73, 122.12, 60.69, 59.93, 48.98, 33.69, 27.20, 21.35, 18.25, 13.34, 12.90.

Odor: milky, floral, creamy, sandalwood

The invention claimed is:

1. A compound of general Formula (I):

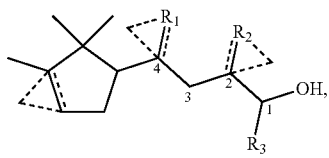

Formula (I)

wherein
$R_1$ represents H, an alkyl or an alkenyl group,
$R_2$ represents an alkyl or an alkenyl group, and
$R_3$ represents H or an alkyl group;
wherein at the position of the dotted lines there is optionally a C=C double bond or a cyclopropane ring; and
wherein the butyl chain C1 to C4 is either saturated or is unsaturated and contains one double bond in position C2/C3 or C3/C4;
wherein the compound comprises either
at least one cyclopropane substituent attached to the butyl chain in position C2 or C4; or
at least one alkenyl group attached to the butyl chain in position C2 or C4, wherein if the alkenyl group is attached to the butyl chain in position C4, the butyl chain comprises a C=C double bond in position C2/C3 or a further alkenyl group in position C2;
or at least one stereoisomer of the compound of general Formula (I); or
a compound of general Formula (VI):

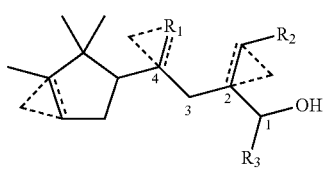

Formula (VI)

wherein
$R_1$ represents H, an alkyl or an alkenyl group,
$R_2$ represents H or an alkyl, and
$R_3$ represents H or an alkyl group;

wherein at the position of the dotted lines there is optionally a C=C double bond or a cyclopropane ring; and
wherein the butyl chain C1 to C4 is either saturated or is unsaturated and contains one double bond in position C2/C3 or C3/C4;
wherein the compound comprises either
at least one cyclopropane substituent attached to the butyl chain in position C2 or C4; or
at least one alkenyl group attached to the butyl chain in position C2 or C4, wherein if the alkenyl group is attached to the butyl chain in position C4, the butyl chain comprises a C=C double bond in position C2/C3 or wherein if the alkenyl group is attached to the butyl chain in position C2, the butyl chain comprises a C=C double bond in position C3/C4; or
an alkyl group attached to the butyl chain in position C2 and C4, wherein the butyl chain comprises a C=C double bond in position C2/C3;
or at least one stereoisomer of the compound of general Formula IV.

2. The compound according to claim 1, wherein the alkyl group is a methyl, ethyl, propyl or butyl group and the alkenyl group is an ethenyl, propenyl or butenyl group.

3. The compound according to claim 1, wherein the compound is present in the form of:
(a) a pure optically active enantiomer;
(b) a racemic mixture of the enantiomers; or
(c) an optically active mixture of various enantiomers.

4. The compound according to claim 1, wherein the compound of general Formula (I) is selected from the group of the following compounds:

| Compound No. | Structure |
|---|---|
| A | ![structure] ...OH |
| A1 | ![structure] ...OH |
| B | ![structure] ...OH |
| B1 | ![structure] ...OH |
| C | ![structure] ...OH |
| D | ![structure] ...OH |

-continued

| Compound No. | Structure |
|---|---|
| E | 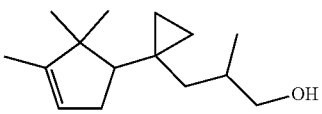 |
| F | 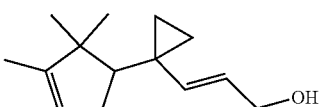 |
| G | 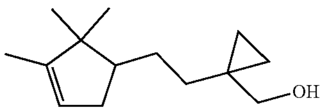 |
| I | 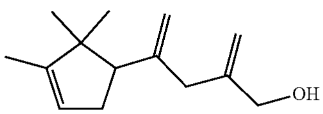 |
| J | 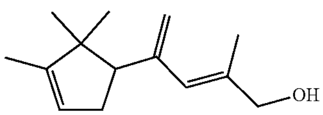 |
| K | 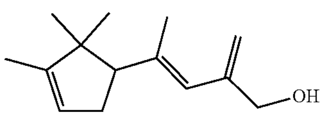 |
| L | 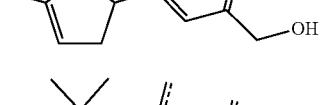 | and their stereoisomers, their enantiomers, and a mixture of any two or more of the compounds, their stereoisomers, and/or their enantiomers; and/or wherein the compound of general Formula (VI) is selected from the group of the following compounds:

| Compound No. | Structure |
|---|---|
| M | 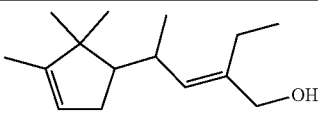 |
| N | 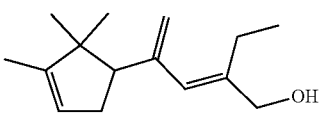 [SMILES: C=C(/C=C(\CC)CO)C1CC=C(C)C1(C)C] |
| O | 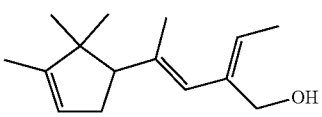 | and their stereoisomers, their enantiomers, and a mixtures of any two or more of the compounds M, N, and O, their stereoisomers, and/or their enantiomers.

5. A fragrance composition comprising at least one compound according to claim 1 and at least one further fragrance substance.

6. A method for producing a compound of general Formula (I) or a mixture of compounds of general Formula (I) according to claim 1, comprising the steps of:
(1-i) preparing or providing a compound according to Formula (II) or Formula (III)

Formula (II)

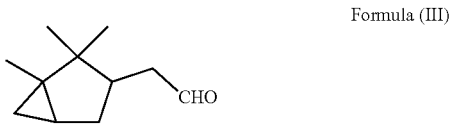

Formula (III)

or their enantiomers;

(1-ii) converting the compound of Formula (II) or Formula (III) or their enantiomers under Baylis-Hillmann conditions to obtain the intermediate (1)

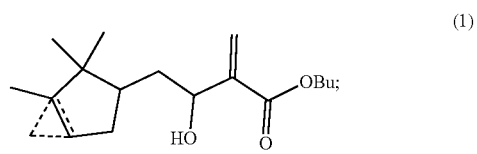

(1)

and (1-iii) after step (1-ii), removing the hydroxyl group using MsCl (methanesulphonyl chloride (mesyl chloride)) or TsCl (tosyl chloride) and TEA (triethylamine), followed by reduction with LAH (lithium aluminium hydride) to obtain compound A or B or their enantiomers

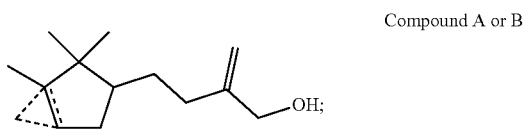

Compound A or B or (1-iv) after step (1-ii), converting the intermediate (1) by a Corey-Chaykovsky reaction to obtain the intermediate (2)

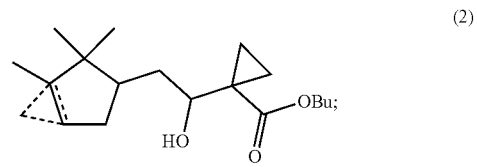

(2)

and (1-v) removing the hydroxyl group using MsCl (methanesulphonyl chloride (mesyl chloride)) or TsCl (tosyl chloride) and TEA (triethylamine), followed by reduction with LAH (lithium aluminium hydride) to obtain compound C or G or their enantiomers

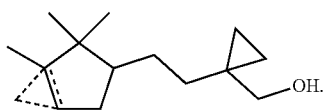

Compound C or G

7. A method for producing a compound of general Formula (I) or a mixture of compounds of general Formula (I) according to claim 1, comprising the steps of:

(2-i) preparing or providing a compound according to Formula (II) or Formula (III)

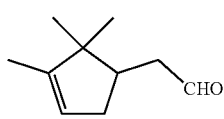

Formula (II)

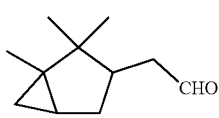

Formula (III)

or their enantiomers;

(2-ii) reacting the compound of Formula (II) or Formula (III) or their enantiomers with paraformaldehyde to give the α-methylene campholene aldehyde (3)

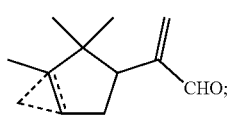

(3)

(2-iii) after step (2-ii), converting the α-methylene campholene aldehyde (3) under Baylis-Hillman conditions to intermediate (3a)

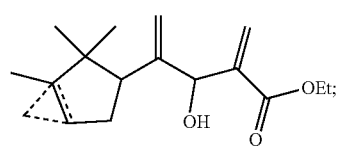

(3a)

and (2-iv) removing the hydroxyl group using MsCl (methanesulphonyl chloride (mesyl chloride)) or TsCl (tosyl chloride) and TEA (triethylamine), followed by reduction with LAH (lithium aluminium hydride) to obtain compound I or J or K or L or their enantiomers

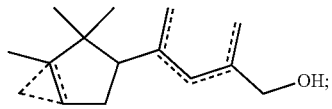

Compound I or J or K or L or (2-v) after step (2-ii), selective cyclopropanating of α-methylene campholene aldehyde (3) under Corey-Caykovsky conditions to obtain the cyclopropanated aldehyde (4)

(4)

(2-vi) reacting the cyclopropanated aldehyde (4) under Horner-Wadsworth-Emmons (HWE) conditions to obtain the alkene (5)

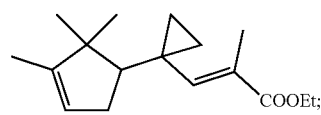

(5)

and (2-vii) after step (2-vi), reducing the alkene (5) with LAH (lithium aluminium hydride) to obtain compound D or its enantiomers

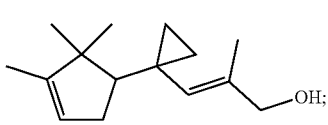

Compound D or (2-viii) after step (2-vi), hydrogenating the alkene (5) using Pd/C, followed by reduction with LAH (lithium aluminium hydride) to obtain compound E or its enantiomers

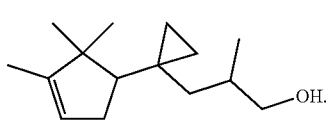

Compound E

8. A method for producing a compound of general Formula (I) or a mixture of compounds of general Formula (I) according to claim 1, comprising the steps of:

(3-i) preparing or providing a compound according to Formula (II) or Formula (III)

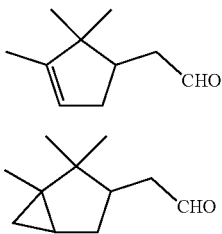

Formula (II)

Formula (III)

or their enantiomers;

(3-ii) reducing the compound of Formula (II) or Formula (III) or their enantiomers to obtain an alcohol (6)

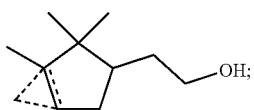

(6)

(3-iii) halogenating the alcohol (6) by an Apple reaction using triphenylphosphine and tetrahalomethanes to obtain the halogen derivative (7)

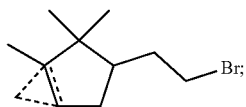

(7)

and (3-iv) reacting the halogen derivative (7) with Mg, CuI and propargyl alcohol to obtain compound A or B or their enantiomers

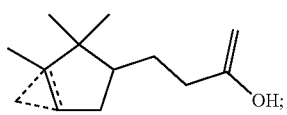

Compound A or B or (3-v) after step (3-i) applying a Knoevenagel condensation reaction to the compound of Formula (II) or Formula (III) or their enantiomers using dimethyl malonate to obtain the dimethyl malonate derivative (8)

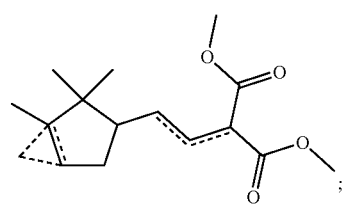

(8)

(3-vi) reducing the dimethyl malonate derivative (8) with LAH (lithium aluminium hydride) to obtain compound A or B or their enantiomers

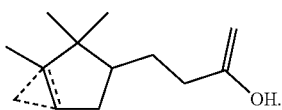

Compound A or B

9. A method for producing a compound of general Formula (I) or a mixture of compounds of general Formula (I) according to claim 1, comprising the steps of:

(4-i) preparing or providing a compound according to Formula (II) or Formula (III)

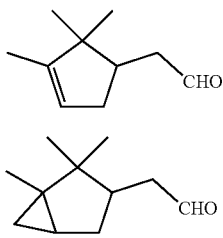

Formula (II)

Formula (III)

or their enantiomers;

(4-ii) reacting the compound of Formula (II) or Formula (III) or their enantiomers with paraformaldehyde to give the α-methylene campholene aldehyde (3)

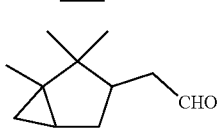

(3)

(4-iii) hydrogenating the α-methylene campholene aldehyde (3), followed by Horner-Wadsworth-Emmons (HWE) and selective hydrogenation to give intermediate (10)

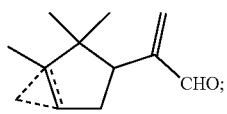

(10)

(4-iv) after step (4-iii) reducing intermediate (10) to the corresponding campholene aldehyde (12) by using DIBAL (diisobutylaluminiumhydrid) or sodium-bis(2-methoxyethoxy)-aluminium (route 1)

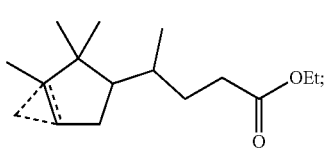

(12)

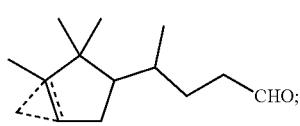

or (4-v) after step (4-iii) reducing intermediate (10) with LAH to give the campholene alcohol (11);

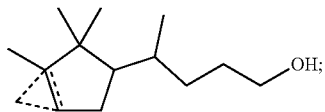
(11)

(4-vi) oxidizing the campholene alcohol (11) using PCC (pyridinium chlorochromate) to obtain the campholene aldehyde (12) (route 2)

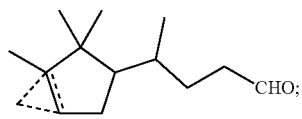
(12)

and (4-vii) after steps (4-iv) or (4-vi), converting the campholene aldehyde (12) with paraformaldehyde to intermediate (13), followed by reduction with LAH (lithium aluminium hydride) to obtain compound A1 or B1 or their enantiomers

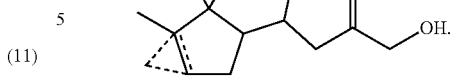
Compound A1 or B1

10. A method of producing, enhancing or modifying a sandalwood odor in a formulation, comprising the following steps:
   providing a compound according to claim 1;
   providing a composition of other constituents; and
   mixing the composition of other constituents with an amount of the compound according to claim 1 which is sufficient
   (a) to produce a sandalwood odor in the resultant complete mixture; or
   (b) to enhance an existing sandalwood odor in the composition of the other constituents; or
   (c) to modify an existing sandalwood odor in the composition of the other constituents.

11. A perfumed product comprising a compound according to claim 1, in an effective amount, and a carrier or substrate.

12. The perfumed product according to claim 11, wherein the perfumed product is a perfume oil, perfume base, formulation for personal hygiene, cleaning agent or laundry agent.

* * * * *